US012268456B2

(12) United States Patent
Harlev et al.

(10) Patent No.: US 12,268,456 B2
(45) Date of Patent: Apr. 8, 2025

(54) SYSTEMS AND METHODS FOR THERAPY ANNOTATION

(71) Applicant: Affera, Inc., Watertown, MA (US)

(72) Inventors: Doron Harlev, Watertown, MA (US); Nadav Geva, Watertown, MA (US); Paul Brian Hultz, Watertown, MA (US); Geoffrey Peter Wright, Watertown, MA (US)

(73) Assignee: AFFERA, INC., Watertown, MA (US)

( * ) Notice: Subject to any disclaimer, the term of this patent is extended or adjusted under 35 U.S.C. 154(b) by 929 days.

(21) Appl. No.: 17/425,274

(22) PCT Filed: Jan. 23, 2020

(86) PCT No.: PCT/US2020/014850
§ 371 (c)(1),
(2) Date: Jul. 22, 2021

(87) PCT Pub. No.: WO2020/154543
PCT Pub. Date: Jul. 30, 2020

(65) Prior Publication Data
US 2022/0096174 A1    Mar. 31, 2022

Related U.S. Application Data

(60) Provisional application No. 62/796,012, filed on Jan. 23, 2019.

(51) Int. Cl.
*A61B 34/00* (2016.01)
*A61B 17/00* (2006.01)
(Continued)

(52) U.S. Cl.
CPC .......... *A61B 34/25* (2016.02); *A61B 18/1492* (2013.01); *A61B 2017/00128* (2013.01);
(Continued)

(58) Field of Classification Search
CPC ... A61B 34/10; A61B 34/25; A61B 2034/252; A61B 2034/254; A61B 2034/207;
(Continued)

(56) References Cited

U.S. PATENT DOCUMENTS

| 4,734,690 A | 3/1988 | Waller |
| 5,133,336 A | 7/1992 | Savitt |

(Continued)

FOREIGN PATENT DOCUMENTS

| EP | 1793349 A2 | 6/2007 |
| EP | 1837828 A2 | 9/2007 |

(Continued)

OTHER PUBLICATIONS

"Framing (World Wide Web)", published by Wikipeda, [online] https://en.wikipedia.org/wiki/Framing_(World_Wide_Web) (Year: 2018).

(Continued)

*Primary Examiner* — Ronald Hupczey, Jr.
(74) *Attorney, Agent, or Firm* — Tarolli, Sundheim, Covell & Tummino LLP

(57) ABSTRACT

Devices, systems, and methods for generating therapy annotations for display on a graphical user interface are disclosed herein. In some embodiments, therapy annotations can correspond to a location of a tip section of a catheter relative to an anatomical structure of a patient when therapy is delivered to the anatomical structure. One or more properties of the therapy annotations can be based at least in part on signals received from sensors distributed about the tip section of the catheter and/or on other characteristics of therapy delivery. The therapy annotations can be displayed alone or in combination with a three-dimensional surface representation of the anatomical structure, a representation of the catheter, and/or other visual indicia, such as a therapy
(Continued)

contour, a distance from a nearest therapy site and/or the most recent therapy site, and/or a representation of gaps between two therapy sites.

23 Claims, 11 Drawing Sheets

(51) Int. Cl.
 *A61B 18/00* (2006.01)
 *A61B 18/14* (2006.01)
 *A61B 34/20* (2016.01)
(52) U.S. Cl.
 CPC .............. *A61B 2018/00779* (2013.01); *A61B 2018/00791* (2013.01); *A61B 2018/00827* (2013.01); *A61B 2018/00875* (2013.01); *A61B 2018/00892* (2013.01); *A61B 2034/2061* (2016.02); *A61B 2034/2063* (2016.02)
(58) Field of Classification Search
 CPC .... A61B 2034/2051; A61B 2034/2053; A61B 2090/374; A61B 2090/376
 See application file for complete search history.

(56) References Cited

U.S. PATENT DOCUMENTS

| | | | |
|---|---|---|---|
| 5,276,785 | A | 1/1994 | Mackinlay et al. |
| 5,364,395 | A | 11/1994 | West |
| 5,391,199 | A | 2/1995 | Ben-Haim |
| 5,433,198 | A | 7/1995 | Desai |
| 5,447,529 | A | 9/1995 | Marchlinski et al. |
| 5,623,583 | A | 4/1997 | Nichino |
| 5,655,535 | A | 8/1997 | Friemel et al. |
| 5,687,737 | A | 11/1997 | Branham et al. |
| 5,797,849 | A | 8/1998 | Vesely et al. |
| 5,820,568 | A | 10/1998 | Willis |
| 5,889,524 | A | 3/1999 | Sheehan et al. |
| 6,037,937 | A | 3/2000 | Beaton |
| 6,120,435 | A | 9/2000 | Eino |
| 6,120,496 | A | 9/2000 | Whayne et al. |
| 6,175,655 | B1 | 1/2001 | George, III et al. |
| 6,216,027 | B1 | 4/2001 | Willis |
| 6,256,038 | B1 | 7/2001 | Krishnamurthy |
| 6,271,856 | B1 | 8/2001 | Krishnamurthy |
| 6,304,267 | B1 | 10/2001 | Sata |
| 6,377,865 | B1 | 4/2002 | Edelsbrunner et al. |
| 6,443,894 | B1 | 9/2002 | Sumanaweera et al. |
| 6,556,206 | B1 | 4/2003 | Benson et al. |
| 6,572,611 | B1 | 6/2003 | Falwell |
| 6,664,986 | B1 | 12/2003 | Kopelman et al. |
| 6,961,911 | B2 | 11/2005 | Suzuki |
| 6,968,299 | B1 | 11/2005 | Bernardini et al. |
| 7,023,432 | B2 | 4/2006 | Fletcher et al. |
| 7,092,773 | B1 | 8/2006 | Oliver et al. |
| 7,155,042 | B1 | 12/2006 | Cowan |
| 7,285,117 | B2 | 10/2007 | Krueger |
| 7,315,638 | B2 | 1/2008 | Hara |
| 7,365,745 | B2 | 4/2008 | Olson |
| 7,450,749 | B2 | 11/2008 | Rouet et al. |
| 7,656,418 | B2 | 2/2010 | Watkins et al. |
| 7,714,856 | B2 | 5/2010 | Waldinger et al. |
| 7,894,663 | B2 | 2/2011 | Berg et al. |
| 8,014,561 | B2 | 9/2011 | Farag et al. |
| 8,334,867 | B1 | 12/2012 | Davidson |
| 8,636,729 | B2 | 1/2014 | Brady et al. |
| 8,784,413 | B2 | 7/2014 | Schwartz |
| 8,786,594 | B2 | 7/2014 | Kushwaha et al. |
| 8,817,076 | B2 | 8/2014 | Steen |
| 8,920,368 | B2 | 12/2014 | Sandhu et al. |
| 9,211,160 | B2 | 12/2015 | Pivotto et al. |
| 9,245,382 | B2 | 1/2016 | Zhou et al. |
| 9,256,980 | B2 | 2/2016 | Kirk |
| 9,311,744 | B2 | 4/2016 | Wu et al. |
| 9,358,076 | B2 | 6/2016 | Moll |
| 9,439,736 | B2 | 9/2016 | Olson |
| 9,613,291 | B2 | 4/2017 | Wu et al. |
| 9,888,973 | B2 | 2/2018 | Olson et al. |
| 10,163,252 | B2 | 12/2018 | Harlev |
| 10,376,320 | B2 | 8/2019 | Harlev |
| 2002/0062083 | A1 | 5/2002 | Ohara |
| 2002/0062084 | A1 | 5/2002 | Ohara |
| 2002/0165541 | A1 | 11/2002 | Whitman |
| 2003/0032862 | A1 | 2/2003 | Ota |
| 2003/0060831 | A1 | 3/2003 | Bonutti |
| 2003/0176778 | A1 | 9/2003 | Messing |
| 2003/0189567 | A1 | 10/2003 | Baumberg |
| 2003/0229282 | A1 | 12/2003 | Burdette et al. |
| 2004/0043368 | A1 | 3/2004 | Hsieh |
| 2004/0233222 | A1 | 11/2004 | Lee et al. |
| 2004/0249809 | A1 | 12/2004 | Ramani |
| 2005/0128184 | A1 | 6/2005 | McGreevy |
| 2006/0159323 | A1 | 7/2006 | Sun |
| 2006/0203089 | A1 | 9/2006 | Akimoto |
| 2006/0241445 | A1 | 10/2006 | Altmann et al. |
| 2007/0038088 | A1 | 2/2007 | Rich et al. |
| 2007/0203396 | A1 | 8/2007 | Mccutcheon et al. |
| 2007/0208260 | A1 | 9/2007 | Afonso |
| 2007/0220444 | A1 | 9/2007 | Sunday et al. |
| 2007/0299351 | A1 | 12/2007 | Harlev |
| 2007/0299352 | A1 | 12/2007 | Harlev |
| 2007/0299353 | A1 | 12/2007 | Harlev |
| 2008/0138009 | A1 | 6/2008 | Block |
| 2008/0161681 | A1 | 7/2008 | Hauck |
| 2008/0221425 | A1 | 9/2008 | Olson |
| 2008/0221438 | A1 | 9/2008 | Chen |
| 2008/0270095 | A1 | 10/2008 | Lombaert et al. |
| 2008/0308256 | A1 | 12/2008 | Deborski |
| 2009/0076476 | A1 | 3/2009 | Barbagli et al. |
| 2009/0163810 | A1 | 6/2009 | Kanade et al. |
| 2009/0171274 | A1 | 7/2009 | Harlev |
| 2009/0177111 | A1 | 7/2009 | Miller |
| 2009/0264741 | A1 | 10/2009 | Markowitz |
| 2009/0264742 | A1 | 10/2009 | Markowitz |
| 2009/0281418 | A1 | 11/2009 | Ruitjers et al. |
| 2010/0053208 | A1 | 3/2010 | Menningen et al. |
| 2010/0069921 | A1 | 3/2010 | Miller et al. |
| 2010/0100081 | A1 | 4/2010 | Tuma |
| 2010/0106009 | A1 | 4/2010 | Harlev |
| 2010/0168560 | A1 | 7/2010 | Hauck |
| 2010/0256558 | A1 | 10/2010 | Ols |
| 2010/0259542 | A1 | 10/2010 | Visser et al. |
| 2010/0305427 | A1 | 12/2010 | Huber |
| 2010/0317981 | A1 | 12/2010 | Grunwald |
| 2011/0015533 | A1 | 1/2011 | Cox et al. |
| 2011/0034971 | A1 | 2/2011 | Svanberg |
| 2011/0058653 | A1 | 3/2011 | Baumgart et al. |
| 2011/0060762 | A1 | 3/2011 | Bessette |
| 2011/0112569 | A1 | 5/2011 | Friedman |
| 2011/0144806 | A1 | 6/2011 | Sandhu et al. |
| 2011/0152684 | A1 | 6/2011 | Altmann et al. |
| 2011/0175990 | A1 | 7/2011 | Sato |
| 2011/0236868 | A1 | 9/2011 | Bronstein |
| 2011/0243323 | A1 | 10/2011 | Sato |
| 2012/0004540 | A1 | 1/2012 | Liu et al. |
| 2012/0059249 | A1* | 3/2012 | Verard .................. A61B 6/463 600/424 |
| 2012/0089038 | A1 | 4/2012 | Ryu |
| 2012/0097178 | A1 | 4/2012 | Helm et al. |
| 2012/0123404 | A1 | 5/2012 | Craig |
| 2012/0165810 | A1 | 6/2012 | Gillberg et al. |
| 2012/0169857 | A1 | 7/2012 | Sato |
| 2012/0174022 | A1 | 7/2012 | Sandhu et al. |
| 2012/0177269 | A1 | 7/2012 | Lu |
| 2012/0221569 | A1 | 8/2012 | Sato |
| 2012/0245465 | A1 | 9/2012 | Hansegard et al. |
| 2013/0002968 | A1 | 1/2013 | Bridge et al. |
| 2013/0030285 | A1 | 1/2013 | Vaillant |
| 2013/0033519 | A1 | 2/2013 | Sato |
| 2013/0129170 | A1 | 5/2013 | Zheng |
| 2013/0241929 | A1 | 9/2013 | Massaeawa et al. |
| 2013/0286012 | A1 | 10/2013 | Medioni |
| 2014/0100453 | A1 | 4/2014 | Kemp |

(56) References Cited

U.S. PATENT DOCUMENTS

| | | |
|---|---|---|
| 2014/0328524 A1 | 11/2014 | Calabrese |
| 2015/0018698 A1 | 1/2015 | Safran |
| 2015/0042657 A1 | 2/2015 | Smith-Casem |
| 2015/0057529 A1 | 2/2015 | Merschon |
| 2015/0119735 A1 | 4/2015 | Yang |
| 2015/0272464 A1 | 10/2015 | Armoundas |
| 2015/0324114 A1 | 11/2015 | Hurley et al. |
| 2016/0000300 A1 | 1/2016 | Williams |
| 2016/0073928 A1 | 3/2016 | Soper et al. |
| 2016/0147308 A1 | 5/2016 | Gelman |
| 2016/0174865 A1 | 6/2016 | Stewart et al. |
| 2016/0196666 A1 | 7/2016 | Venkatraghavan et al. |
| 2016/0242667 A1 | 8/2016 | Fay et al. |
| 2016/0242855 A1 | 8/2016 | Fichtinger et al. |
| 2016/0275653 A1 | 9/2016 | Ross |
| 2016/0331262 A1 | 11/2016 | Kuck et al. |
| 2016/0364862 A1 | 12/2016 | Reicher |
| 2016/0367168 A1 | 12/2016 | Malinin et al. |
| 2017/0038951 A1 | 2/2017 | Reicher |
| 2017/0065256 A1 | 3/2017 | Kim et al. |
| 2017/0079542 A1 | 3/2017 | Spector |
| 2017/0079681 A1 | 3/2017 | Burnside et al. |
| 2017/0202469 A1 | 7/2017 | Scharf |
| 2017/0209072 A1 | 7/2017 | Oren |
| 2017/0245936 A1 | 8/2017 | Kanade et al. |
| 2017/0265943 A1 | 9/2017 | Sela et al. |
| 2017/0301124 A1 | 10/2017 | Dala-Krishna |
| 2017/0323473 A1 | 11/2017 | Wright |
| 2017/0325900 A1 | 11/2017 | Harlev |
| 2017/0325901 A1 | 11/2017 | Harlev |
| 2017/0330487 A1 | 11/2017 | Harlev |
| 2018/0228386 A1 | 8/2018 | McCall |
| 2018/0289435 A1 | 10/2018 | Namiki |
| 2018/0317864 A1 | 11/2018 | Sra et al. |
| 2019/0004621 A1 | 1/2019 | Nuber et al. |
| 2019/0030328 A1 | 1/2019 | Stewart et al. |
| 2019/0096122 A1 | 3/2019 | Harlev |
| 2019/0125422 A1 | 5/2019 | Babkin et al. |
| 2019/0269368 A1 | 9/2019 | Hauck et al. |
| 2020/0196908 A1 | 6/2020 | Ben-Haim et al. |
| 2021/0022623 A1 | 1/2021 | Rice et al. |

FOREIGN PATENT DOCUMENTS

| | | |
|---|---|---|
| EP | 2332461 A1 | 6/2011 |
| WO | 2003039350 A2 | 5/2003 |
| WO | 2005022468 A1 | 3/2005 |
| WO | 2005063125 A1 | 7/2005 |
| WO | 2008107905 A3 | 9/2008 |
| WO | 2008138009 A1 | 11/2008 |
| WO | 2010054409 A1 | 5/2010 |
| WO | 2017192746 A1 | 11/2017 |
| WO | 2017192781 A1 | 11/2017 |
| WO | 2017197114 A1 | 11/2017 |
| WO | 2017197247 A2 | 11/2017 |
| WO | 2017197294 A1 | 11/2017 |
| WO | 2018092063 A1 | 5/2018 |
| WO | 2018200865 A1 | 11/2018 |
| WO | 2019046376 A2 | 3/2019 |

OTHER PUBLICATIONS

3D-Doctor User's Manual: 3D Imaging, Modeling and Measurement Software (2012) (pp. 1-269) ("3D Doctor").
Bernardini, Fausto et al., "The Ball-Pivoting Algorithm for Surface Reconstruction", IEEE transactions on visualization and computer graphics 5.4 (1999), Oct. 1999, pp. 349-359.
Carr, J.C. et al., "Reconstruction and Representation of 3D Objects with Radial Basis Functions", Proceedings of the 28th annual conference on Computer graphics and interactive techniques. ACM, 2001, 10 Pages.
Chen, Yang et al., "Description of Complex Objects from Multiple Range Images Using an Inflating Balloon Model", Computer Vision and Image Understanding 61.3, May 1995, pp. 325-334.
Curless, Brian et al., "A Volumetric Method for Building Complex Models from Range Images", Proceedings of the 23rd annual conference on Computer graphics and interactive techniques. ACM, 1996, 10 Pages.
Davis, James et al., "Filling holes in complex surfaces using volumetric diffusion", 3D Data Processing Visualization and Transmission, 2002. Proceedings. First International Symposium on. IEEE, 2002, 15 Pages.
Elfes, Alberto, "Using Occupancy Grids for Mobile Robot Perception and Navigation", Computer, vol. 22, Issue: 6, Jun. 1989, pp. 46-57.
Gelas, Arnaud et al., "Surface Meshes Smoothing", Insight Journal. Feb. 20, 2009, 6 pages.
Hilbert, Sebastian et al., "Real-Time Magnetic Resonance-guided ablation of typical right atrial flutter using a combination of active catheter tracking and passive catheter visualization in main: initial results from a consecutive patient series", Aug. 27, 2015, 6 pages.
ISA, "PCT Application No. PCT/US17/30877 International Search Report and Written Opinion mailed Jul. 14, 2017", 9 pages.
ISA, "PCT Application No. PCT/US17/30928 International Search Report and Written Opinion mailed Jul. 25, 2017", 12 pages.
ISA, "PCT Application No. PCT/US17/32160 International Search Report and Written Opinion mailed Aug. 21, 2017", 8 pages.
ISA, "PCT Application No. PCT/US17/32378 Invitation to Pay Additional Fees and Partial Search Report mailed Oct. 23, 2017", 12 pages.
ISA, "PCT Application No. PCT/US17/32378 International Search Report and Written Opinion mailed Dec. 20, 2017", 15 pages.
ISA, "PCT Application No. PCT/US17/32459 International Search Report and Written Opinion mailed Jul. 21, 2017", 9 pages.
ISA, "PCT Application No. PCTUS18/48460, International Search Report and Written Opinion mailed Feb. 1, 2019", 19 pages.
ISA, "PCT Application No. PCTUS20/14850, International Search Report and Written Opinion mailed Apr. 7, 2020", 14 pages.
Kazhdan, Michael et al., "Poisson Surface Reconstruction", Eurographics Symposium on Geometry Processing, 2006, 10 Pages.
Lange et al., 3D Ultrasound-CT registration of the liver using combined landmark-intensity information, International Journal of Computer Assisted Radiology and Surgery, 4(1):79-88, 2008.
Lempitsky, Victor, "Surface Extraction from Binary Volumes with Higher-Order Smoothness", Computer Vision and Pattern Recognition (CVPR), 2010 IEEE Conference on. IEEE, Jun. 2010, 6 Pages.
Liang, Jian et al., "Robust and Efficient Implicit Surface Reconstruction for Point Clouds Based on Convexified Image Segmentation", Journal of Scientific Computing 54.2-3, 2013, pp. 577-602.
Lounsbery, Michael et al., "Parametric Surface Interpolation", IEEE Computer Graphics and Applications 12.5 (1992) Sep. 1992, pp. 45-52.
Schroeder, William et al., "Flying Edges: A High-Performance Scalable Isocontouring Algorithm", IEEE Xplore, Oct. 2015, 8 pages.
Sethian, J.A., "Level Set Methods and Fast Marching Methods", Cambridge University Press, 1996, 21 Pages.
Wang, Jianning et al., "A Hole-Filling Strategy for Reconstruction of Smooth Surfaces in Range Images", Computer Graphics and Image Processing, 2003. SIBGRAPI 2003. XVI Brazilian Symposium on. IEEE, Oct. 2003, 7 pages.
Zhao, Hong-Kai et al., "Fast Surface Reconstruction Using the Level Set Method", Variational and Level Set Methods in Computer Vision, 2001. Proceedings. IEEE Workshop on. IEEE, Jul. 2001, 8 pages.

\* cited by examiner

SYSTEMS AND METHODS FOR THERAPY ANNOTATION

CROSS REFERENCE TO RELATED APPLICATIONS

The present application is a 35 U.S.C. § 371 U.S. National Phase application of International Application No. PCT/US2020/014850, filed Jan. 23, 2020, which claims the benefit of U.S. Provisional Patent Application No. 62/796,012, filed Jan. 23, 2019, which are both incorporated herein by reference in their entireties.

BACKGROUND

Three-dimensional models can be used to assist in the placement or use of a device when such placement or use is not easily observable or practical. For example, in medical procedures, three-dimensional models are used to assist in the placement and use of medical devices for diagnosis or treatment of patients. An example of such a medical procedure carried out with the assistance of a three-dimensional model is the use of a catheter to deliver radio frequency ("RF") ablation to form lesions that interrupt abnormal conduction in cardiac tissue, thus terminating certain arrhythmias in the heart.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

A. Overview

Figure 1:
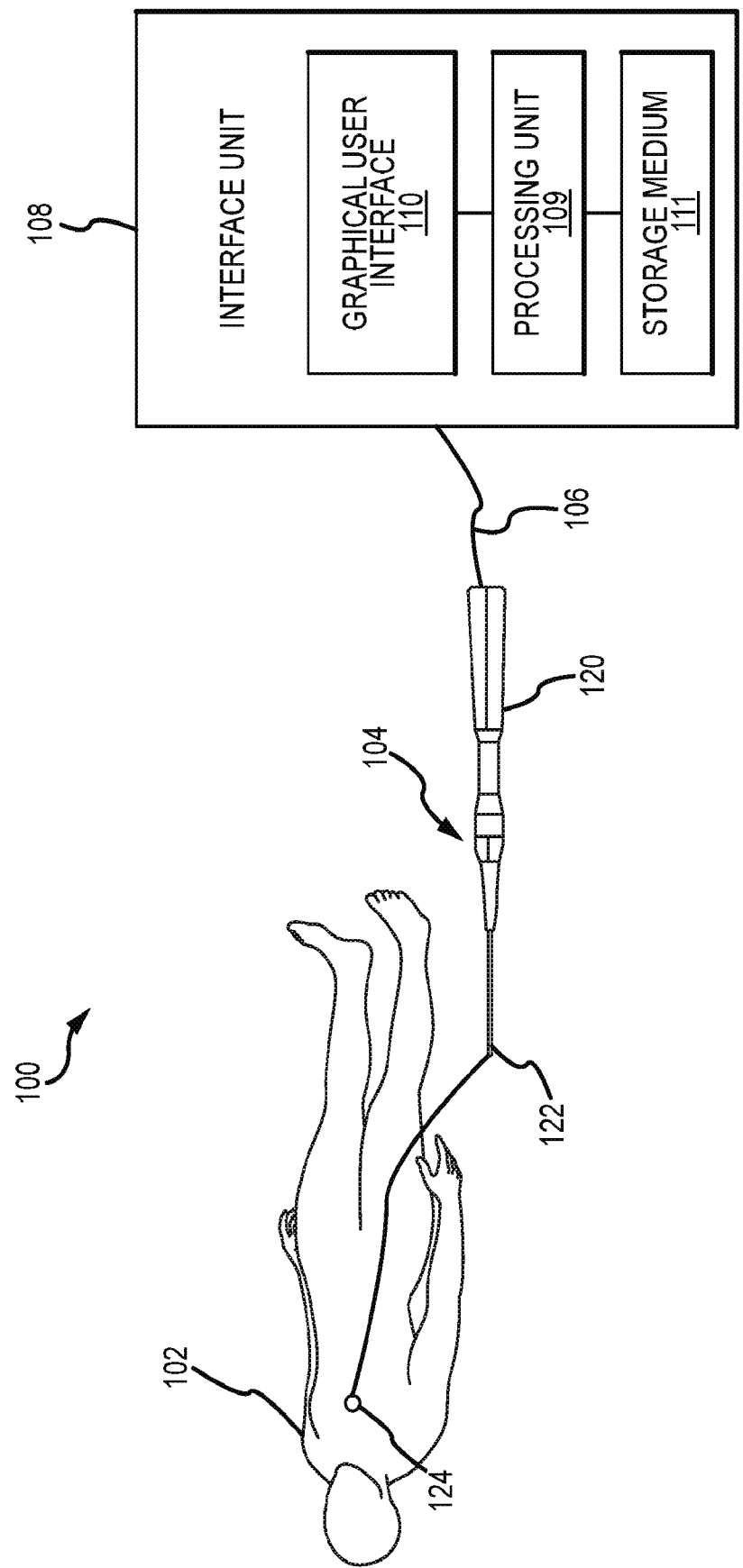
FIG. 1 is a schematic representation of a system for treating a human patient and configured in accordance with various embodiments of the present technology.

Point-by-point therapy delivery can be used to treat several patient conditions. For example, a minimally-invasive radiofrequency (RF) catheter can be used in a patient's heart to treat certain arrhythmias In this scenario, the RF catheter can be used to form one or more discrete points (e.g., discrete lesions) on the wall of the patient's heart by applying energy (e.g., electrical energy) to the wall. The applied energy damages tissue at the treatment site(s), decreasing the tissue's electrical activity. In turn, abnormal electrical signals can be prevented from propagating through the damaged tissue, thereby preventing arrhythmias In many cases, discrete regions of therapy delivery must be connected to form a contiguous region (e.g., contour, surface, volume, etc.) on an anatomical structure of a patient. For example, a contiguous contour along a surface of a patient's heart can isolate a patient's pulmonary vein in the left atrium of the patient's heart to treat paroxysmal atrial fibrillation. Gaps between the discrete regions formed during treatment can decrease the treatment's effectiveness, render the treatment entirely ineffective, and/or lead to other complications.

Accurately positioning a medical device within an anatomical structure of a patient and/or effectively delivering therapy to desired locations within and/or on the anatomical structure can prove challenging. For example, although a physician can often track the general or relative position of a medical device within an anatomical structure using a conventional tracking and/or mapping system, it is often not readily apparent to the physician which surfaces of the medical device and/or of the anatomical structures are in contact with and/or are proximate to each other. Thus, although a physician may know the position of the medical device within the anatomical structure and/or may know that the medical device is proximate to the anatomical structure, the physician can be uncertain regarding whether the medical device is proximate to the anatomical structure at a desired location and/or orientation on a wall of the anatomical structure and/or whether the medical device is proximate to the anatomical structure at another location (e.g., on a nearby, adjacent wall of the anatomical structure). This can lead to uncertainty regarding the size, orientation, and/or position of a lesion formed on the anatomical structure. Moreover, it is often not readily apparent using conventional systems whether gaps exist between discrete regions of therapy until after treatment is completed, meaning that some patients must undergo a follow-up treatment procedure before the therapy is successful.

In contrast with these conventional systems, the following disclosure is directed to devices, systems, and methods of generating annotations on a three-dimensional model of an anatomical structure of a patient to facilitate, for example, precisely positioning a medical device within the anatomical structure and delivering therapy across a contiguous region (e.g., a contiguous contour, surface, volume, etc.) on the anatomical structure. More specifically, three-dimensional annotations can be displayed relative to a location of a medical device (e.g., the tip section of a catheter) within an anatomical structure. The three-dimensional annotations can be used alone or in combination with other three-dimensional information, such as with a three-dimensional surface representation of an anatomical structure. In some embodiments, a three-dimensional annotation can represent the location of the tip section of the medical device within the anatomical structure when therapy was delivered. In these and other embodiments, three-dimensional annotations can display various information based at least in part on signals received from sensors distributed about the tip section of the medical device. For example, the three-dimensional annotations can display (i) information regarding proximity between the medical device and the anatomical structure (e.g., which portion of the tip section of the medical device and/or which surface of an anatomical structure are/were in contact and/or close proximity); (ii) information relating to tissue characteristics (e.g., impedance, temperature, etc.) at a location on the anatomical structure; (iii) information (e.g., location, size, shape, orientation, etc.) relating to a lesion formed at a location on an anatomical structure; (iv) information (e.g., power, voltage, current, etc.) regarding energy delivered to a location on an anatomical structure; and/or (v) other information, such as distance from nearest therapy site, whether discrete therapy regions overlap and/or are connected, and/or time of therapy (e.g., start time, stop time, how recently therapy was applied to a site, etc.). In these and still other embodiments, the present technology can provide information that aids a physician in determining whether treatment is successful. In this manner, the present technology facilitates accurately positioning a medical device within an anatomical structure of a patient and accurately delivering therapy to locations within the anatomical structure. In turn, the present technology can increase the effectiveness and/or success rate of point-by-point therapy treatments, often obviating the need for patients to undergo a follow-up therapy procedure.

Specific details of several embodiments of the present technology are described herein with reference to FIGS. 1-12. Although many of the embodiments are described with respect to devices, systems, and methods of generating annotations relative to a three-dimensional model of a heart of a patient, other applications and other embodiments in addition to those described herein are within the scope of the present technology. For example, unless otherwise specified or made clear from context, the devices, systems, and methods of the present technology can be used for any of various medical procedures, such as procedures performed on a hollow anatomical structure of a patient, and, more specifically, in a hollow anatomical structure in which direct visual access to the medical procedure is impractical and/or is improved by the use of a model of the anatomical structure. Thus, for example, the systems, device, and methods of the present disclosure can be used to facilitate visualization of a medical device inserted into a heart cavity as part of a medical treatment associated with diagnosis, treatment, or both of a cardiac condition (e.g., cardiac arrhythmia) Additionally, or alternatively, the devices, systems, and methods of the present disclosure can be used in one or more medical procedures associated within interventional pulmonology, brain surgery, or sinus surgery (e.g., sinuplasty).

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in an anatomical chamber. As used herein, the term "patient" should be considered to include human and/or non-human (e.g., animal) patients upon which a medical procedure is being performed.

B. Selected Embodiments of Therapy Annotation Devices, Systems, and Methods

1. Therapy Annotation Devices and Systems

FIG. 1 is a schematic representation of a system 100 for treating a human patient 102 and configured in accordance with an embodiment of the present technology. In the arrangement shown in FIG. 1, the system 100 is being used to perform a medical procedure (e.g., an ablation treatment) on the patient 102. The system 100 can include a medical device 104 connected via an extension cable 106 to an interface unit 108. The interface unit 108 (e.g., a catheter interface unit) can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109. The storage medium 111 can have stored thereon computer executable instructions for causing the one or more processors of the processing unit 109 to carry out one or more portions of the various methods described herein, unless otherwise indicated or made clear from context. In some embodiments, the system 100 can include one or more other components, such as a mapping system, a recording system, an irrigation pump, a generator, and/or one or more return electrodes attached to the skin of the patient 102.

As described in further detail below, the graphical user interface 110 can be used as part of diagnosis and/or treatment of tissue of an anatomical structure (e.g., a heart) of the patient 102 by, for example, generating and/or displaying three-dimensional annotations relative to the location of a tip section 124 of the medical device 104. The three-dimensional annotations generated and/or displayed in accordance with various embodiments of the present technology can be used alone or in combination with other three-dimensional information, such as with a three-dimensional surface representation of the anatomical structure. In some embodiments, for example, a three-dimensional annotation can represent the current location of the tip section 124 of the medical device 104 within the anatomical structure and/or the location of the tip section 124 within the anatomical structure when therapy was delivered. In these and other embodiments, three-dimensional annotations can display various information based, at least in part, on signals received from sensors 126 distributed about the tip section 124 of the medical device 104. In this manner, the present technology is expected to provide a physician with improved spatial context for three-dimensional movement and/or proximity of the medical device 104 relative to one or more surfaces of the anatomical structure.

As a specific example, generating and/or displaying the three-dimensional annotations alone or in combination with the three-dimensional model on the graphical user interface 110 during therapy according to any one or more of the methods described herein can facilitate three-dimensional movement of the medical device 104 within the anatomical structure to create one or more lesions in a desired pattern on one or more surfaces of the anatomical structure represented by the three-dimensional model. In turn, the present technology is expected to increase the effectiveness and/or success rate of point-by-point therapy treatments, often obviating the need for patients to undergo a follow-up therapy procedure.

Figure 2:
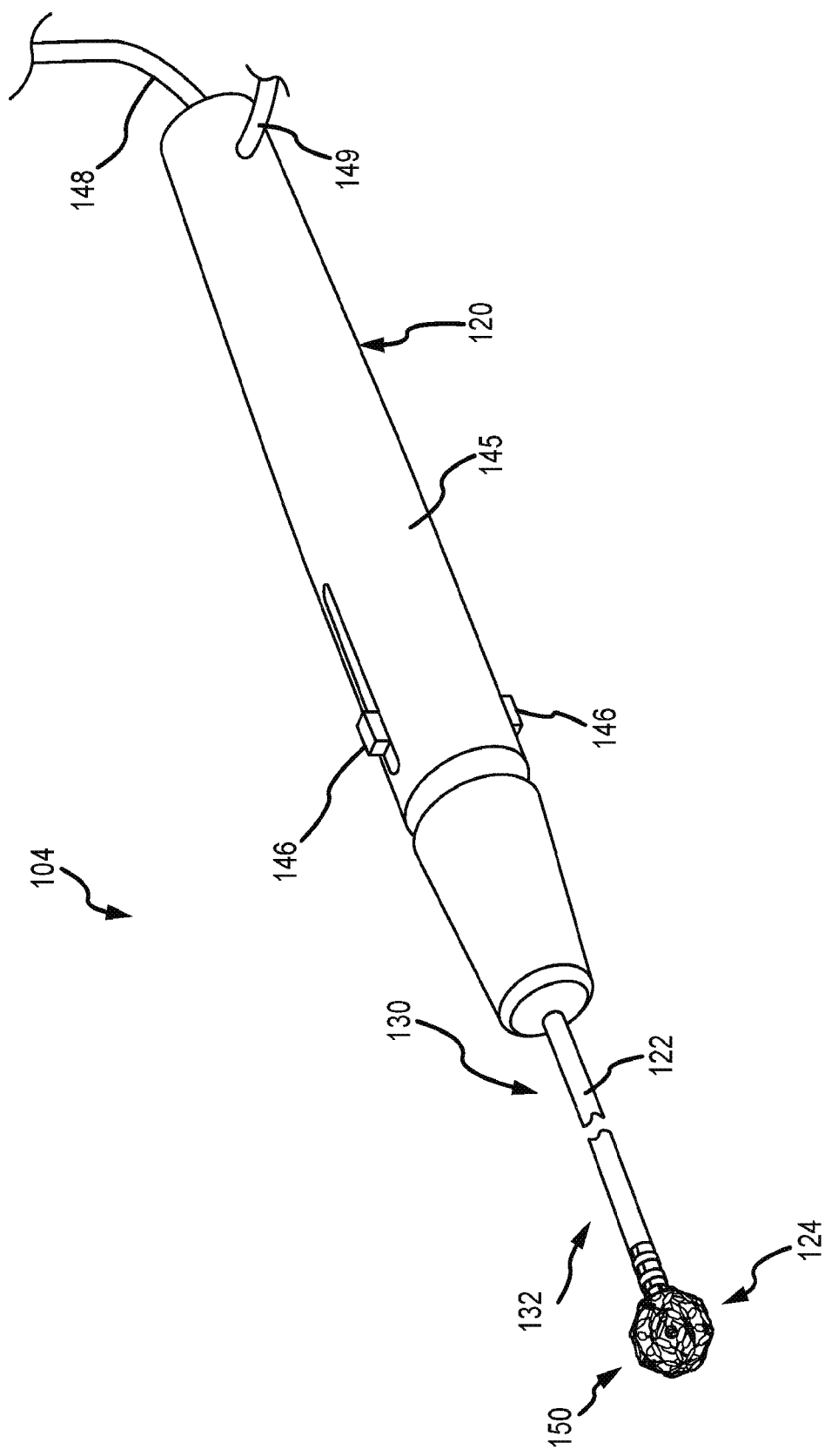
FIG. 2 is a perspective view of an exemplary medical device of the system of FIG. 1 configured in accordance with various embodiments of the present technology.
Figure 3:
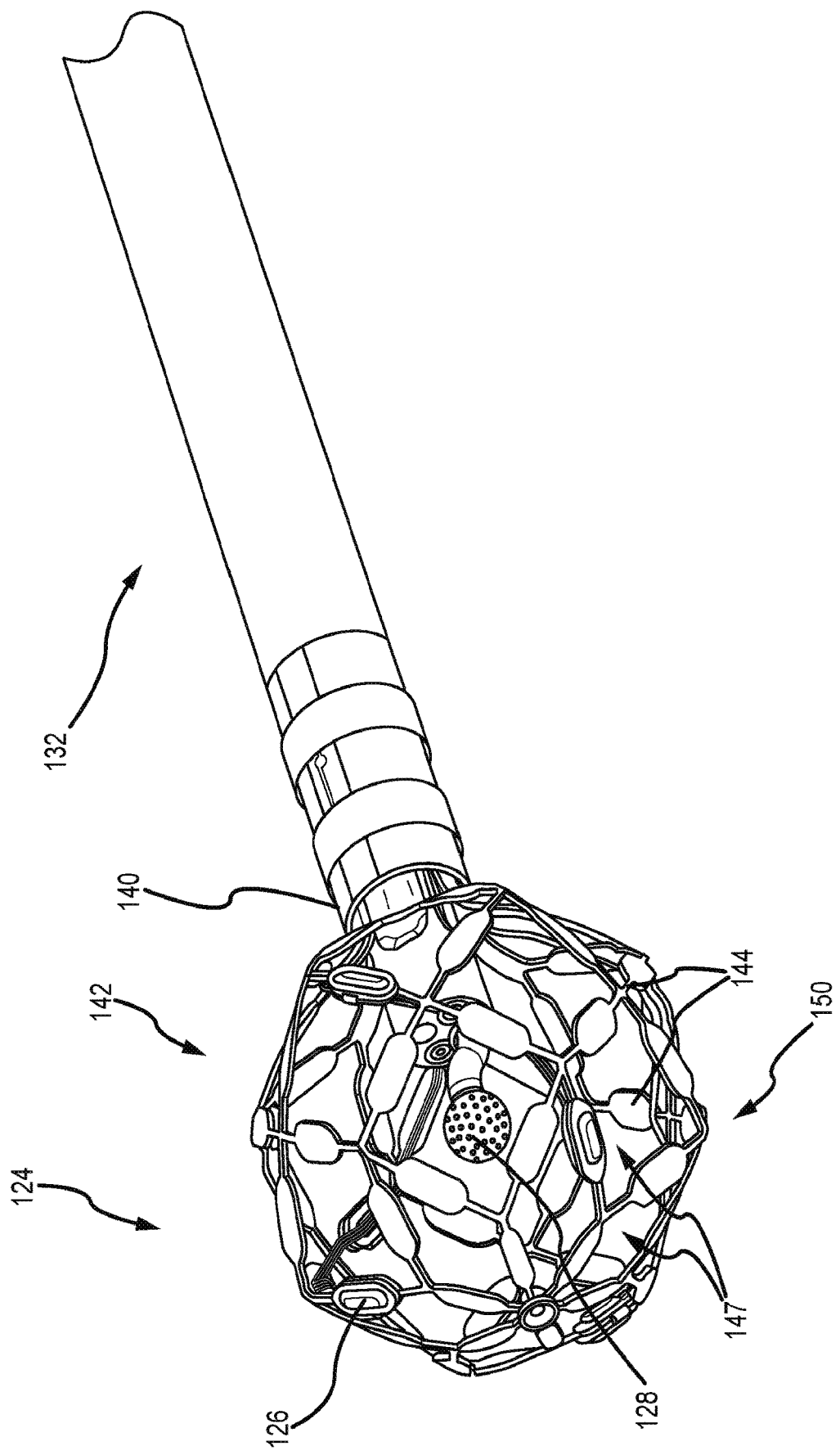
FIG. 3 is a schematic representation of a tip section of the medical device of FIG. 2 and configured in accordance with various embodiments of the present technology.

FIG. 2 is a perspective view of the medical device 104 of the system 100 of FIG. 1, and FIG. 3 is a schematic representation of a tip section 124 of the medical device 104. Referring to FIGS. 1-3 together, the medical device 104 can be any of various different medical devices known in the art (e.g., for diagnosis, treatment, or both). In the illustrated embodiment, for example, the medical device 104 is a catheter 104. Thus, the medical device 104 can include a handle 120, a shaft 122, a tip section 124, and/or an irrigation element 128. The handle 120 can be coupled to a proximal end portion 130 of the shaft 122. The tip section 124 and/or the irrigation element 128 can be coupled to a distal end portion 132 of the shaft 122 opposite the proximal end portion 130. In some embodiments, the shaft 122 can define a lumen that can be in fluid communication with an irrigation pump (not shown). Additionally, or alternatively, the shaft 122 can include electrical wires extending along the shaft 122 to carry signals between the tip section 124 and the handle 120.

The handle 120 can include a housing 145 and an actuation portion 146. In use, the actuation portion 146 can be operated to deflect a distal end portion 132 of the shaft to facilitate positioning the tip section 124 into contact with tissue at a treatment site. The handle 120 can further, or instead, be coupled to a fluid line connector 149 and/or to an electrical connector 148 for delivery of irrigation fluid, electrical signals, and/or energy (e.g., electrical energy), respectively, along the shaft 122 to/from the tip section 124 (e.g., to/from an electrode 150 and/or to/from one or more sensors 126 of the tip section 124).

The tip section 124 generally includes any portion of the catheter 104 that directly or indirectly engages tissue for the purpose of treatment, diagnosis, or both and, therefore, can include all manner and type of contact and/or non-contact interaction with tissue known in the art. For example, the tip section 124 can include contact and/or non-contact interaction with tissue in the form of energy interaction (e.g., electrical energy, ultrasound energy, light energy, and any combinations thereof) and further, or instead, can include measurement of electrical signals emanating from tissue. Thus, for example, the tip section 124 can deliver energy (e.g., electrical energy) to tissue in the anatomical structure as part of any number of procedures including treatment (e.g., ablation, electroporation, etc.), diagnosis (e.g., mapping), or both.

In the illustrated embodiments, the tip section 124 includes a coupling portion 140 and a deformable portion 142. As used herein, the terms "expandable" and "deformable" are used interchangeably, unless otherwise specified or made clear from the context. Thus, for example, it should be understood that the deformable portion 142 is expandable unless otherwise specified. The coupling portion 140 is secured to the distal end portion 132 of the shaft 122, and the deformable portion 142 can extend distally from the coupling portion 140.

The deformable portion 142 of the tip section 124 can be deformed for delivery and expanded at a treatment site to have a cross-sectional dimension larger than a cross-sectional dimension of the shaft 122. Further, in an expanded state, the deformable portion 142 of the tip section 124 is deformable upon sufficient contact force with tissue. As described in greater detail below, the shape and extent of the deformation of the deformable portion can be detected based at least in part on signals received from sensors 126 of the tip section 124. In some embodiments, the deformable portion 142 can be radiopaque such that deformation of the deformable portion 142 as a result of contact with tissue is observable, for example, through X-Ray or similar visualization techniques. The detection and/or observation of the deformation of the deformable portion 142 of the tip section 124 can, for example, provide improved certainty that an intended treatment is, in fact, being provided to tissue. It should be appreciated that improved certainty of positioning of an electrode 150 with respect to tissue can reduce the likelihood of gaps in a lesion pattern and, also or instead, can reduce the time and number of lesions otherwise required to avoid gaps in a lesion pattern.

The deformable portion 142 of the tip section 124 can include an electrode 150 (e.g., an ablation electrode 150, an electroporation electrode 150, etc.). In some embodiments, the deformable portion 142 can include struts 144 joined together to form the electrode 150. In the illustrated embodiment, the plurality of struts 144 are joined to collectively define a plurality of cells 147. In other embodiments, however, the struts 144 can be joined in accordance with methods known in the art. Additionally, or alternatively, at least some of the struts 144 can be coupled to the coupling portion 140 of the tip section 124 to secure the deformable portion 142 to the distal end portion 132 of the shaft 122. The struts 144 can be moveable relative to one another. More specifically, the struts 144 can be flexible to one another such that the deformable portion 142 can move between a compressed state, in the presence of external force, and an uncompressed state, in the absence of external force (e.g., in embodiments where the deformable portion 142 is self-expandable).

In general, the struts 144 of the electrode 150 can be dimensioned and arranged relative to one another for delivery of substantially uniform current density about the deformable portion 142 of the tip section 124. The struts 144 can be electrically coupled to the electrical connector 148 (e.g., via one or more wires (not shown) extending along the shaft 122).

The electrode 150 is a continuous structure about the deformable portion 142 that acts as one electrode in a monopolar electrode configuration. It should be appreciated, however, that the electrode 150 can include electrically isolated portions about the deformable portion 142 such that the electrode 150 includes two electrodes of a bipolar electrode configuration. In use, energy (e.g., electrical energy) can be delivered to the electrode 150 to ablate or otherwise treat (e.g., via electroporation) tissue (e.g., in contact with the electrode 150). As compared to smaller electrodes, the electrode 150 can provide wider lesions, facilitating the creation of a pattern of overlapping lesions (e.g., reducing the likelihood of arrhythmogenic gaps, and reducing the time and number of lesions required for an overlapping pattern, or both). Additionally, or alternatively, the larger electrode 150 can facilitate the delivery of more power for providing wider and deeper lesions.

In these and other embodiments, the electrode 150 can be an electroporation electrode configured to apply one or more electrical pulses to cells of tissue. For example, the catheter 104 can be configured to apply pulsed field energy (e.g., reversible electroporation, irreversible electroporation, pulsed electrical fields, etc.) and/or another form of energy to tissue at a treatment site via the electrode 150 of the tip section 124. As a more specific example, the catheter 104 can be configured to deliver monophasic or biphasic pulses with high voltage (e.g., between about 500 volts and 4000 volts) and short duration (e.g., between 100 nanoseconds and 100 microseconds) to the electrode 150.

Additionally, or alternatively, the catheter 104 can be configured to deliver various forms of pulse trains of energy to tissue at a treatment site via the electrode 150 of the tip section 124. For example, the catheter 104 can deliver energy to tissue either continuously or as a train of tightly (e.g., temporally) spaced pulses followed by a suspension period during which no energy is delivered to the tissue. At the end of the suspension period, the catheter 104 can again deliver energy to tissue either continuously or as a train of tightly spaced pulses followed by another suspension period. The catheter 104 can repeat this cycle as needed. In still other embodiments, the catheter 104 can vary the amount of current delivered during either continuous energy delivery or during delivery of different pulses (e.g., pulses of a pulse train).

As best seen in FIG. 3, the tip section 124 and/or the deformable portion 142 can include one or more sensors 126. For example, the tip section 124 can include one or more of electrodes, thermistors, ultrasound transducers, optical fibers, image sensors, and/or other types of sensors. In use, the sensors 126 can be used in one or more modes of parameter measurement. For example, the sensors 126 can measure temperature, electrogram characteristics (e.g., amplitude), force, ultrasound, impedance, location (e.g., motion during therapy), shape of the deformable portion 142 (e.g., during deployment or deformation), shape of an anatomical structure, energy (e.g., power, voltage, current, impedance), and/or other parameter measurements. These parameters vary over time, producing time-varying signals that can be measured by the interface unit 108.

Sensors 126 can be mounted about (e.g., along) the deformable portion 142 of the tip section 124 (e.g., mounted onto one of the struts 144 of the deformable portion 142) and can be electrically insulated from the electrode 150. In general, the sensors 126 can be positioned along one or both of the inner portion and the outer portion of the deformable portion 142. For example, sensors 126 can extend through a portion of the deformable portion 142. Such positioning of the sensors 126 through a portion of the deformable portion 142 can facilitate measuring conditions along the outer portion and the inner portion of the electrode 150 and/or of the deformable portion 142. As a specific example, one or more of the sensors 126 can include a flexible printed circuit, a thermistor secured between portions of the flexible printed circuit, and a termination pad opposite the thermistor. A sensor 126 can be mounted on the deformable portion 142 of the tip section 124 with the thermistor disposed along an outer portion of the deformable portion 142 and the termination pad disposed along the inner portion of the deformable portion 142. In certain instances, the thermistor can be disposed along the outer portion to provide an accurate indication of tissue temperature.

The sensors 126 can be substantially uniformly spaced from one another (e.g., in a circumferential direction and/or in an axial direction) about the deformable portion 142 when the deformable portion 142 is in an uncompressed state. Such substantially uniform distribution of the sensors 126 can, for example, facilitate determining an accurate deformation and/or temperature profile of the deformable portion 142 during use. In some embodiments, one or more sensors 126 can include a radiopaque portion and/or a radiopaque marker to facilitate visualization (e.g., using fluoroscopy) of the sensor 126 during use.

In these and other embodiments, one or more sensors 126 of the medical device 104 (e.g., of the tip section 124) can further be a magnetic position sensor. The magnetic position sensor can be any of various magnetic position sensors well known in the art and can be positioned at any point along the distal end portion 132 of the shaft 122 and/or at any point along the tip section 124. The magnetic position sensor can, for example, include one or more coils that detect signals emanating from magnetic field generators. One or more coils for determining position with five or six degrees of freedom can be used. The magnetic field detected by the magnetic position sensor can be used to determine the location (e.g., position, orientation, and/or shape) of the tip section 124 and/or of the distal end portion 132 of the shaft 122 according to one or more methods commonly known in the art such as, for example, methods based on using a magnetic sensor to sense magnetic fields and using a look-up table to determine location of the magnetic position sensor. Accordingly, because the tip section 124 is coupled to the distal end portion 132 of the shaft 122 in a known, fixed relationship to the magnetic position sensor, the magnetic position sensor can also provide the location (e.g., position, orientation, and/or shape) of the tip section 124. While the location of the tip section 124 is described as being determined based on magnetic position sensing, other position sensing methods can additionally or alternatively be used. For example, the location (e.g., position, orientation, and/or shape) of the tip section 124 can be additionally, or alternatively, based on impedance, ultrasound, and/or imaging (e.g., real time MRI or fluoroscopy). Furthermore, a location of the tip section 124 should be understood to include, for example, a smoothed and/or filtered position, orientation, and/or shape.

In some embodiments, one or more wires (not shown) extend from each sensor 126 along the inner portion of the deformable portion 142 and into the shaft 122. The one or more wires can be in electrical communication with the interface unit 108 (FIG. 1) such that each sensor 126 can send electrical signals to and receive electrical signals from the interface unit 108 during use. In this regard, one or more sensors 126 can act as an electrode (e.g., a surface electrode) to detect electrical activity of an anatomical structure in an area local to the sensor 126. For example, each sensor 126 can form part of an electrode pair useful for detecting contact between each sensor 126 and tissue. For example, electrical energy (e.g., current) can be driven through each sensor 126 and another electrode (e.g., any one or more of various different electrodes described herein), and a change in a measured signal (e.g., voltage or impedance) can be indicative of the presence of tissue. Because the position of the tip section 124 is known, detection of contact through respective measured signals at the sensors 126 can be useful for determining portions of the deformable portion 142 proximate to tissue and/or for determining a shape of an anatomical structure in which the tip section 124 is disposed during the course of a medical procedure.

In use, each sensor 126 can, further or instead, act as an electrode to detect electrical activity of an anatomical structure local to the respective sensor 126, with the detected electrical activity forming a basis for an electrogram with the respective sensor 126 and, further or instead, can provide lesion feedback. The sensors can be arranged such that electrical activity detected by each sensor 126 can form the basis of unipolar electrograms and/or bipolar electrograms. Additionally, or alternatively, the sensors 126 can cooperate with a center electrode, for example, to provide near-unipolar electrograms. For example, a sensor 126 can be disposed along the irrigation element 128 and can act as the center electrode. Additionally, or alternatively, the irrigation element 128 can act as a center electrode itself. In these and still other embodiments, one or more other sensors can be disposed along the irrigation element 128, such as one or more image sensors.

As discussed above, the medical device 104 can include an irrigation element 128. As best seen in FIG. 3, for example, in the illustrated embodiment the irrigation element 128 includes a stem and bulb. The bulb of the irrigation element 128 can define one or more irrigation holes in fluid communication with the stem, and the stem can be coupled to the distal end portion 132 of the shaft 122 and can be in fluid communication with the fluid line connector 149 via the lumen of the shaft 122 and the handle 120. Accordingly, irrigation fluid can pass through the lumen defined by the shaft 122, through the stem, and can exit the irrigation element 128 through the irrigation holes defined by the bulb.

The bulb can be substantially spherical to facilitate directing irrigation fluid toward substantially the entire inner portion of the deformable portion 142. It should be appreciated, however, that the bulb can be any of various different shapes that facilitate multi-directional dispersion of irrigation fluid toward the inner portion of the deformable portion 142. Moreover, the irrigation element 128 can be spaced relative to the inner portion of the deformable portion 142 such that the irrigation holes direct irrigation fluid toward the inner portion of the deformable portion 142 in an expanded state. In particular, given that the deformable portion 142 of the tip section 124 in some embodiments is intended to contact tissue during ablation, the irrigation holes can be oriented toward the inner portion of the deformable portion 142 in contact with the tissue. In certain implementations, the irrigation holes can be spaced circumferentially and axially about the irrigation element 128. For example, the irrigation holes can be spatially distributed along the bulb with at least a portion of the irrigation holes arranged to direct irrigation fluid in a distal direction with respect to the tip section 124 and at least a portion of the irrigation holes arranged to direct irrigation fluid in a proximal direction with respect to the tip section 124. More generally, the irrigation holes can be distributed to produce a relatively uniform dispersion of irrigation fluid along the inner portion of the deformable portion 142 enveloping the irrigation element 128. Directing the irrigation fluid toward the deformable portion 142 of the tip section 124 in this way can, for example, reduce the likelihood of unintended tissue damage resulting from an ablation treatment.

2. Three-Dimensional Models of Anatomical Structures

In certain implementations, the delivery of energy from the tip section 124 to tissue can rely upon proximity between the tip section 124 and the tissue. In such implementations, it may be particularly desirable for the graphical user interface 110 to display a three-dimensional model of the medical device 104 (e.g., of the tip section 124) and/or an anatomical structure to provide the physician with knowledge of the location (e.g., position, orientation, and/or shape) of the tip section 124 relative to one or more surfaces of the anatomical structure. It should be further appreciated that the devices, systems, and methods of the present disclosure can be implemented using any number and manner of designs of the medical device 104 that rely upon, or at least derive some benefit from, knowledge of location of the tip section 124 relative to one or more surfaces of the anatomical structure.

Referring to FIGS. 1-5 together, a three-dimensional representation 532 (FIG. 5) of an anatomical structure 432 (e.g., an anatomical cavity, such as a heart cavity) of the patient 102 can be constructed based on known locations of the tip section 124 of the medical device 104 in the anatomical structure 432 (e.g., prior to, during, and/or after application of energy to tissue of the anatomical structure 432) and additionally, or alternatively, based on images (e.g., segmented CT or MR images) of the anatomical structure 432 (FIG. 4) acquired prior to or during the procedure. For example, if the tip section 124 of the medical device 104 is movable in blood in the anatomical structure 432 and obstructed only by a surface 433 (FIG. 4) of the anatomical structure 432, the known positions of the tip section 124 of the medical device 104 can be taken together to provide an indication of a blood-tissue boundary of the anatomical structure 432, and this blood-tissue boundary can form a basis for the three-dimensional representation 532 of the anatomical structure 432. In some embodiments, the three-dimensional representation 532 can be a triangular mesh or non-uniform rational basis spline surface.

In general, a three-dimensional model 544 (FIG. 5) can be projected onto the graphical user interface 110. The three-dimensional model 544 can include the three-dimensional representation 532 of the anatomical structure 432 and/or a representation 504 (FIG. 5) of the medical device 104. The representation 504 of the medical device 104 can include, for example, a depiction of the tip section 124 at a location (e.g., position, orientation, and/or shape) determined based on signals received from sensors 126 (e.g., from a magnetic position and/or other sensors) distributed about the tip section 124. By way of example and not limitation, the representation 504 can include one or more of the following: an icon; an outline; a two-dimensional geometric shape such as a circle; and a three-dimensional geometric shape such as a sphere. Additionally, or alternatively, the representation 504 of the medical device 104 can include a three-dimensional depiction of the tip section 124. Continuing with this example, the three-dimensional representation 504 of the tip section 124 can be at least partially based on knowledge of the size and shape of the tip section 124. Thus, for example, in implementations in which the deformable portion 142 of the tip section 124 is deformed through contact with a surface of an anatomical structure, the deformation of the deformable portion 142 can be shown in the three-dimensional representation 504 of the tip section 124.

It should be appreciated that the three-dimensional model 544 has utility as, among other things, an analog for the position of the tip section 124 of the medical device 104 in the anatomical structure 432. That is, the location (e.g., position, orientation, and/or shape) of the tip section 124 of the medical device 104 relative to the surface 433 of the anatomical structure 432 is known (e.g., based on signals received by the interface unit 108 from sensors 126, such as from a magnetic position sensor) and can be represented on the graphical user interface 110 at a corresponding location within the three-dimensional representation 532 of the anatomical structure 432. Thus, for example, as the tip section 124 moves within the anatomical structure 432 during a medical procedure, the representation 504 of the medical device 104 can be depicted on the graphical user interface 110 as undergoing analogous, or at least similar, movements relative to the three-dimensional representation 532 of the anatomical structure 432 in the three-dimensional model 544. Given this correspondence between the three-dimensional model 544 and the physical aspects of the medical procedure, it should be appreciated that displaying images of the three-dimensional model 544 on the graphical user interface 110 can be a useful visualization tool for the physician as the physician moves the tip section 124 of the medical device 104 in the anatomical structure 432.

Figure 4:
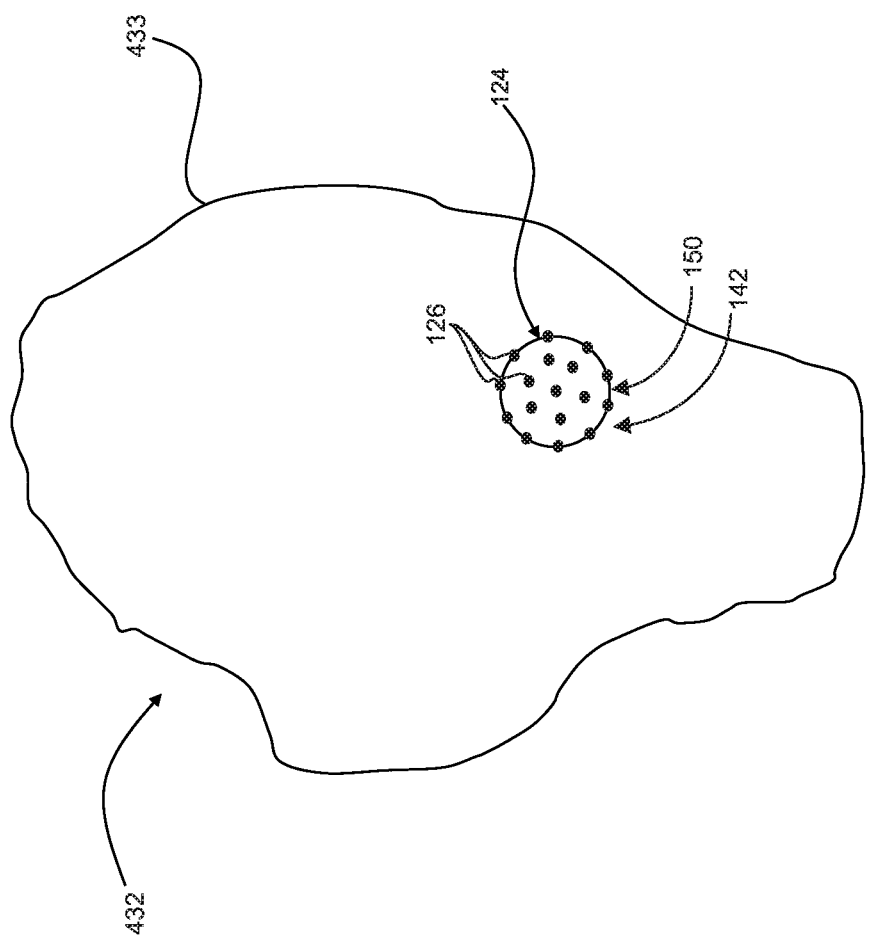
FIG. 4 is a schematic representation of a medical device within an anatomical structure of a patient in accordance with various embodiments of the present technology.
Figure 5:
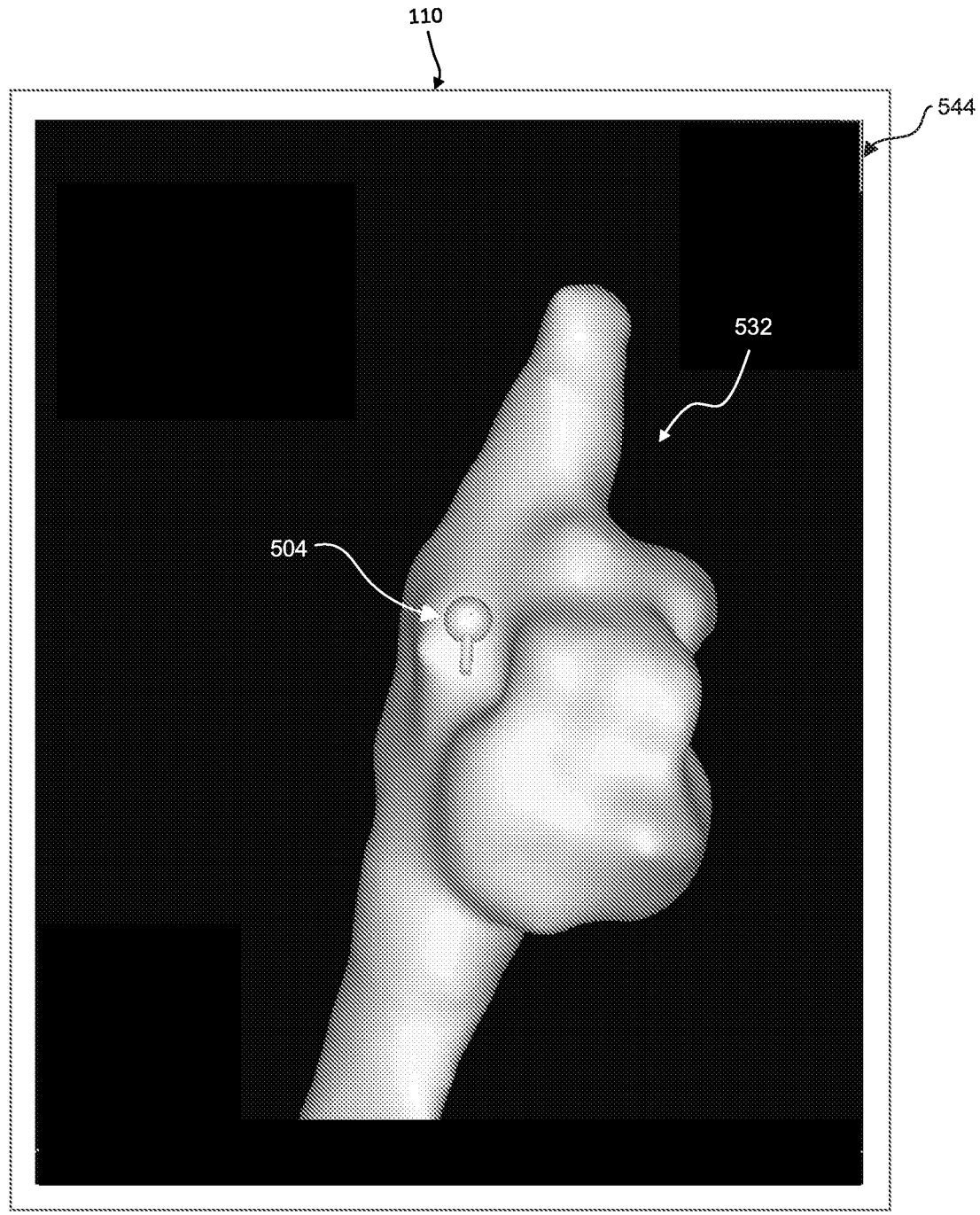
FIG. 5 is a graphical user interface of the system of FIG. 1 displaying a projection of a three-dimensional model during a medical procedure and configured in accordance with various embodiments of the present technology.

As best seen in FIGS. 4 and 5, in one specific treatment example, the tip section 124 can be placed adjacent to the surface 433 of the anatomical structure 432 and energy (e.g., RF energy) can be directed from the electrode 150 of the tip section 124 to the surface 433 of the anatomical structure 432 to ablate or otherwise treat (e.g., deliver electroporation therapy to) tissue at a treatment site. In implementations in which the anatomical structure 432 is a heart structure, such treatment along the surface 433 of the anatomical structure 432 can, for example, treat cardiac arrhythmia in patients with this condition. However, the effectiveness of the lesions created using the tip section 124 along the surface 433 of the anatomical structure 432 can be dependent upon the location (e.g., position, orientation, and/or shape) of the lesions. Accordingly, the multi-dimensional visualization of the location of the medical device 104 (facilitated by displaying images of the three-dimensional model 544 according to any one or more of the methods described herein) can be useful for the efficient and effective mapping of the heart and/or efficient and effective delivery of ablation treatment to treat cardiac arrhythmia.

3. Therapy Annotations

Referring again to FIGS. 1-5, in point-by-point therapy delivery embodiments where the tip section 124 of the medical device 104 is used to deliver discrete regions of therapy to the anatomical structure 432, it may be particularly desirable for the graphical user interface 110 to display one or more therapy annotations or tags alone or in combination with the three-dimensional representation 532 of the anatomical structure 432 and/or the representation 504 of the medical device 104 to provide the physician with various information relating to past and/or present regions of therapy delivery. It should be further appreciated that the devices, systems, and methods of the present disclosure can be implemented using any number and manner of designs of the medical device 104 that rely upon, or at least derive some benefit from, knowledge of location of the tip section 124 relative to one or more surfaces of the anatomical structure.

In general, as discussed above, the tip section 124 of the medical device 104 of the present technology can provide larger contact regions between the electrode 150 of the deformable portion 142 and the anatomical structure 432 as compared to conventional medical devices, and can include sensors 126 (e.g., electrogram sensors, temperature sensors, etc.) distributed about the tip section 124. The larger structure of the tip section 124 is expected to provide useful, spatially-distributed information that is not otherwise available using smaller, conventional medical device tips. For example, as discussed above and in greater detail below, each of the sensors 126 can provide information pertaining to only an area local to the respective sensor 126. Thus, based at least in part on signals received from one or more of the sensors 126 distributed about the tip section 124, the devices, system, and methods of the present technology can generate and/or display a map of therapy annotations or tags representative of information relevant to a physician, such as (i) information pertaining to (e.g., current or past) locations (e.g., positions, orientations, and/or shapes) of the tip section 124; (ii) information regarding proximity between the medical device 104 and the anatomical structure 432 (e.g., which portion of the tip section 124 of the medical device 104 and/or which surface of an anatomical structure 432 are/were in contact and/or close proximity); (iii) information relating to tissue characteristics (e.g., impedance, temperature, etc.) at a location on the anatomical structure 432; (iv) information (e.g., location, size, shape, orientation, etc.) relating to a lesion formed at a location on an anatomical structure 432; (v) information (e.g., power, voltage, current, etc.) regarding energy delivered to a location on an anatomical structure 432; and/or (vi) other information, such as distance from a nearest therapy site, whether discrete therapy regions overlap and/or are connected, and/or time of therapy delivery (e.g., start time, stop time, how recently therapy was applied to a site, etc.).

FIGS. 6-9 are images 660, 770, 880, and 990, respectively, of the model 544 that can be displayed on the graphical user interface 110 in accordance with various embodiments of the present technology. For the sake of efficient and clear description, all references in this section to the medical device 104 and to the anatomical structure 432 refer to features first described and/or discussed above with reference to FIGS. 1-4. As shown in FIGS. 6-9, the model 544 in each of the images 660, 770, 880, and 990 can include the representation 532 of the anatomical structure 432 and the representation 504 of the medical device 104 (e.g., of the tip section 124 and/or the shaft 122 of the medical device 104). In some embodiments, the representation 504 of the medical device 104 can depict the current location of the medical device 104 within the anatomical structure 432 in accordance with the discussion above. Thus, for example, as the tip section 124 moves within the anatomical structure 432 during a medical procedure, the representation 504 of the medical device 104 can be depicted on the graphical user interface 110 as undergoing analogous, or at least similar, movements relative to the three-dimensional representation 532 of the anatomical structure 432 in the three-dimensional model 544.

In some embodiments, the model 544 can include one or more indicia with properties (e.g. size, position, color, pattern, continuity, transparency, etc.) that vary depending on the relative location (e.g., position, orientation, and/or shape) of the representation 504 of the medical device 104 with respect to the three-dimensional representation 532 of the anatomical structure 432. For example, proximity rings 653 and 655 shown in FIG. 6 can be projected onto the three-dimensional representation 532 of the anatomical structure 432 in a direction of shortest distance between the representation 504 of the medical device 104 and the three-dimensional representation 532 of the anatomical structure 432. Continuing with this example, the size of the outer proximity ring 655 relative to the three-dimensional representation 532 of the anatomical structure 432 can vary with the distance between the representation 504 of the medical device 104 and the three-dimensional representation 532 of the anatomical structure 432. Other properties of the proximity rings 653 and 655 and/or other visual indicia (e.g., a ring 657 shown in FIG. 6) can vary depending on other types of information such as, e.g., signals indicative of contact, proximity, and/or temperature, or, additionally or alternatively, the direction of articulation of the shaft 122 of the medical device 104.

Figure 6:
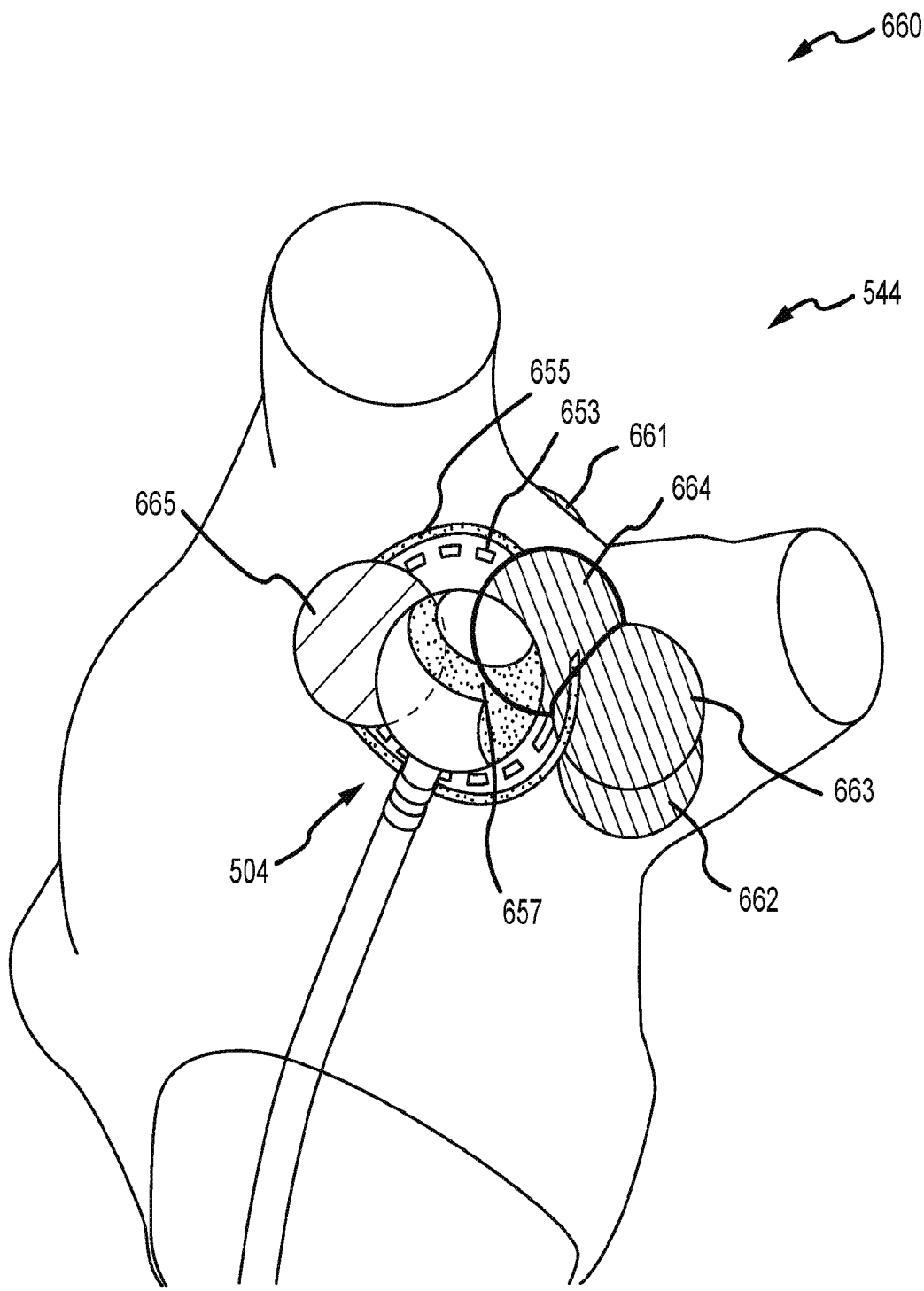
FIGS. 6-10 are images of a three-dimensional model illustrating various visual indicia that can be generated and/or displayed in accordance with various embodiments of the present technology.

Additionally, or alternatively, the model 544 can include one or more therapy annotations. In some embodiments, for example, one or more therapy annotations can be displayed independently (e.g., in three dimensions) or can be projected onto a three-dimensional surface, such as the representation 532 of the anatomical structure 432. Referring to FIG. 6, for example, five three-dimensional therapy annotations (individually labeled 661-665) are shown in the image 660. The therapy annotations 661-665 can represent a location of the tip section 124 of the medical device 104 relative to the anatomical structure 432 when therapy was delivered to tissue of the anatomical structure 432. For example, the therapy annotation 661 is shown at a position within the representation 532 of the anatomical structure 432 that is located further into the page than the therapy annotations 663, 664, and 665. Thus, a physician is able to view where therapy has been delivered to the anatomical structure 432. In other words, therapy annotations in combination with a representation 532 of the anatomical structure 432 can provide a physician spatial information related to regions of the anatomical structure 432 that have been treated.

In some embodiments, the location of a therapy annotation displayed in the model 544 can depend on other parameters in addition to or in lieu of the location of the medical device 104 relative to the anatomical structure 432 when therapy was delivered. For example, the location of a therapy annotation can be discounted or ignored during periods of time when the tip section 124 of the medical device 104 may be displaced (e.g., due to the patient's respiration or heartbeat). In these and other embodiments, multiple locations of the tip section 124 of the medical device 104 can be combined over time into a single therapy annotation (e.g., through smoothing or filtering) to reduce errors in location (e.g., due to the patient's respiration or heartbeat). In these and still other embodiments, a physician and/or user can adjust the time range during which therapy annotations are determined, generated, and/or displayed.

In some embodiments, the therapy annotations can be generated and/or displayed in substantially real-time. For example, the therapy annotations can be displayed as soon as therapy is delivered to a region of the anatomical structure 432 (or shortly thereafter considering processing time). In these and other embodiments, therapy annotations can be generated and/or displayed during or after the time period in which therapy is delivered to a region of the anatomical structure.

Figure 7:
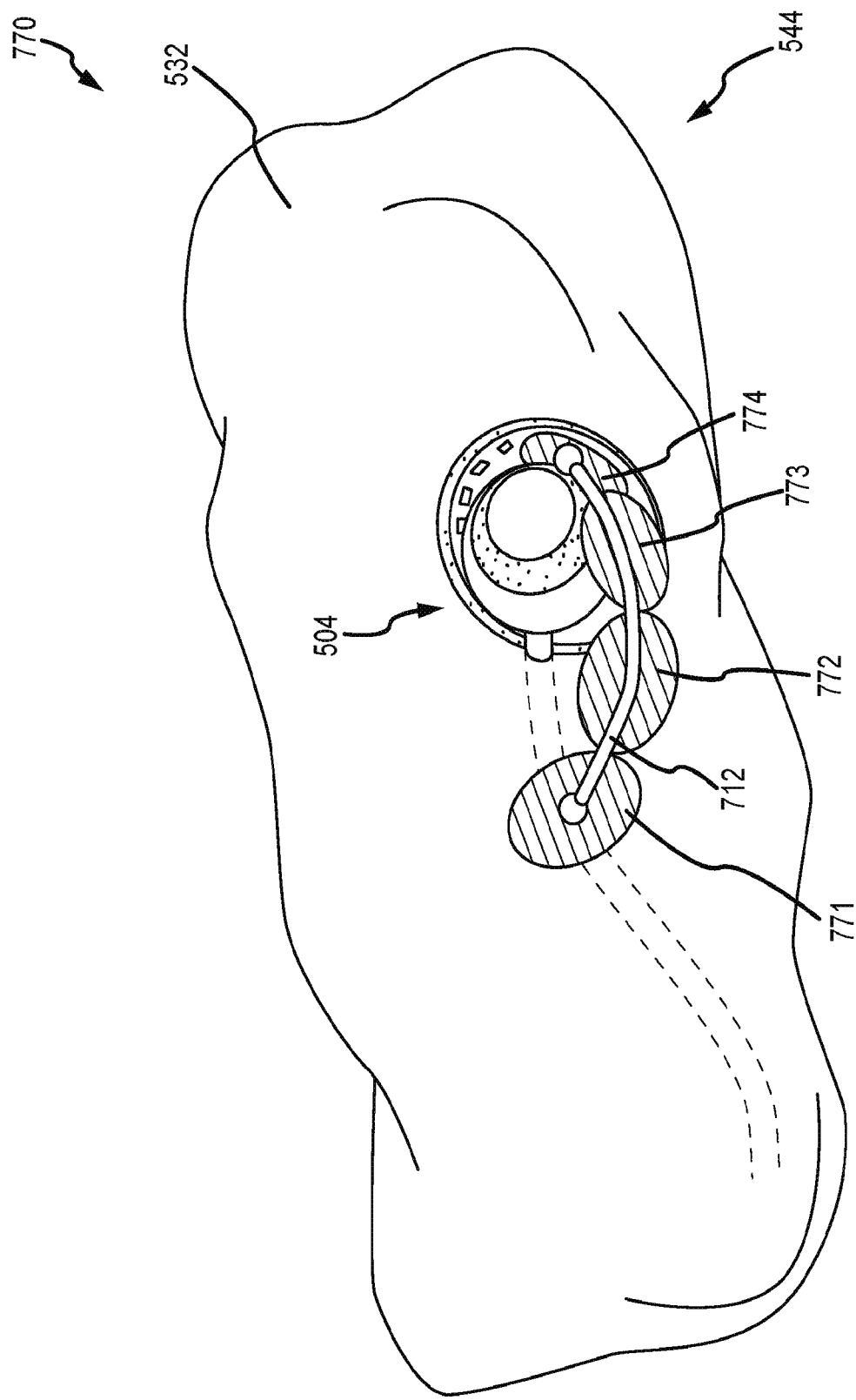

Although the therapy annotations 661-665 are shown in FIG. 6 as symmetric balls or globes roughly corresponding to the general, uncompressed shape of the deformable portion 142 of the medical device 104, therapy annotations in other embodiments can have different shapes. For example, the therapy annotations can be flattened disks (as shown by the therapy annotations 771-774 in FIG. 7), ellipsoids, or other shapes having one dimension that is substantially smaller than two orthogonal dimensions of the shape. Additionally, or alternatively, therapy annotations within the same model 544 can have varying and/or asymmetric shapes, sizes, and/or orientations. For example, the therapy annotations 771-774 in FIG. 7 are displayed with various orientations. More specifically, the therapy annotations 771-774 are displayed with orientations that correspond to a plane tangential to a surface of the medical device 104 during a time period when therapy was delivered at these locations. In this manner, the display of the therapy annotations 771-774 can collectively indicate to a physician that the surface 433 of the anatomical structure 432 is concave relative to the medical device 104 at locations within the anatomical structure 432 corresponding to the location of the therapy annotations 771-774 within the representation 532 of the anatomical structure 432.

In some embodiments, properties of the therapy annotations can be determined based at least in part on signals received from sensors 126 distributed about the tip section 124 of the medical device 104. For example, the interface unit 108 can determine the shape, size, position, and/or orientation of a therapy annotation based at least in part on which of the sensors 126 on the tip section 124 measured signals indicative of successful therapy delivery. In some embodiments, the interface unit 108 can determine which subset of the sensors 126 indicate successful therapy delivery by monitoring temperature measurements captured and relayed to the interface unit 108. For example, the interface unit 108 can determine that a sensor 126 that measures an increase in temperature (e.g., above a threshold temperature or change in temperature and/or for a threshold period of time) indicated successful therapy delivery. As such, the interface unit 108 can determine not only which portion of the deformable portion 142 of the tip section 124 indicated successful therapy delivery, but also the orientation of the deformable portion 142 against the surface 433 of the anatomical structure. Accordingly, the interface unit 108 can generate and/or display a therapy annotation having a shape, a size, a position, and/or an orientation corresponding to positions of the subset of the sensors 126 indicating successful therapy delivery. As a result, in contrast with merely projecting the tip section 124 onto the representation 532 of the anatomical structure 432 as is often practiced in the art, therapy annotations generated in accordance with various embodiments of the present technology can provide a physician a greater amount of information relating to (i) the portion of the tip section 124 of the medical device 104 indicating successful therapy delivery, (ii) the surface 433 of the anatomical structure 432 at locations within the anatomical structure 432 corresponding to the locations of the therapy annotations within the representation 532 of the anatomical structure 432 and/or (iii) therapy delivered to the anatomical structure 432 at those locations.

In these and other embodiments, a weighting of the sensors 126 can be used to determine a shape, a size, a position, and/or an orientation of a therapy annotation. For example, the interface unit 108 can determine a weighting of each or a subset of the sensors 126 based on an indication of therapy delivery (e.g., successful therapy delivery) such as the examples enumerated above. Continuing with this example, the interface unit 108 can assign a larger weight to a sensor 126 showing a greater indication of therapy delivery (e.g. higher temperature and/or longer time at elevated temperature). Such a weighting can determine the influence that the given sensor 126 has on a shape, a size, a position, and/or an orientation of a therapy annotation. For example, a position and/or an orientation of a flattened shape can be determined as a weighted combination (e.g. a weighted mean) of the positions and/or the orientations of all or a subset of the sensors 126 with weights corresponding to an indication of therapy delivery. Thus, a sensor 126 showing a lesser indication of therapy delivery can, in some embodiments, contribute less to the properties of the therapy annotation than a sensor 126 having a greater indication of therapy delivery.

In these and other embodiments, one or more other measurements and/or parameters in addition to or in lieu of temperature can be used to determine properties of the therapy annotations. For example, the interface unit 108 can determine a shape, size, and/or orientation of a therapy annotation based at least in part on those sensors 126 that detect contact force between the deformable portion 142 and the surface 433 of the anatomical structure 432. In these and other embodiments, the interface unit 108 can determine a shape, size, and/or orientation of a therapy annotation based at least in part on those sensors 126 that register an impedance above a threshold value before therapy delivery and/or on those sensors 126 that register a decrease in impedance above a threshold value when therapy is delivered.

It should be appreciated that therapy annotations with properties corresponding to sensors 126 indicating therapy delivery (e.g., indicating successful therapy delivery) can provide a physician feedback regarding which portions of the anatomical structure 432 are receiving therapy. For example, if the physician intends to deliver therapy to a first portion of the anatomical structure 432, the physician can (during and/or after delivering therapy to the first portion) view a corresponding therapy annotation to ensure that therapy is being and/or was delivered to the first portion of the anatomical structure 432. If the therapy annotation indicates (i) that therapy is not or was not delivered to the first portion and/or (ii) is or was delivered to a second, unintended portion of the anatomical structure 432, the physician can decide whether to continue with therapy delivery, to stop therapy delivery and reposition the tip section 124 of the medical device 104, and/or to return the tip section 124 of the medical device 104 to a location corresponding to the first portion of the anatomical structure 432.

Additionally, or alternatively, the therapy annotations can provide information regarding lesion formation. For example, continuing with the temperate example above, the interface unit 108 can monitor the sensors 126 distributed about the deformable portion 142 of the tip section 124 to determine which of the sensors 126 measured an increase in temperature (e.g., above a threshold temperature or change in temperature and/or for a threshold period of time). Accordingly, the interface unit 108 can display a therapy annotation having size, shape, and/or property corresponding to the sensors 126 that measured an increase in temperature. That is, the model 544 can provide a physician an indication of the size and shape of the lesion formed at a particular location on the surface 433 of the anatomical structure 432 based on which sensors 126 measured an increase in temperature. In these and other embodiments, the interface unit 108 can use one or more other signals captured by the sensors 126 to generate and/or display a therapy annotation indicative of a lesion formed at a corresponding location within the anatomical structure 432. For example, the interface unit 108 can determine information (e.g., power, voltage, current, etc.) regarding energy delivered to tissue of the anatomical structure 432 at a given location within the anatomical structure 432. Based at least in part on this information, for example, the interface unit 108 can increase or change the shape, size, and/or other properties of the therapy annotation generated and/or displayed as the energy (including, e.g., time and/or power) applied to the tissue increases.

Various methods are known in the art for conveying depth information in a view of a three-dimensional representation projected onto a two-dimensional display. For example, a perspective view can render more distant objects smaller and nearer objects larger. Additionally, or alternatively, volume rendering techniques can be applied such that one representation (e.g., a representation 504 of a medical device 104, or a therapy annotation) can be modified by another representation (e.g., a representation 532 of an anatomical structure 432) that is less deep in a two-dimensional projection if the projections of the two representations overlap. For example, object representations (e.g., a representation 504 of a medical device 104, and/or a therapy annotation) located at least partially within or behind a representation 532 of an anatomical structure 432 can be partially obscured by modifying properties of the object representation (e.g., an intensity, color, pattern, shade, saturation, hue, transparency, etc. of one or more portions of the representation 504 of the medical device 104) as a function of (i) a depth within the representation 532 of the anatomical structure 432 and/or (ii) a depth relative to one or more surfaces of the representation 532 of the anatomical structure 432. Thus, as a specific example, as a representation 504 of a medical device 104 passes through a surface of the representation 532 of the anatomical structure 432, properties of the representation 504 of the medical device 104 can change, and these properties can further change as a depth of the representation 504 of the medical device 104 varies within the representation 532 of the anatomical structure 432.

The pattern, color, shade, or hue of a therapy annotation can indicate various information to a physician. Referring again to FIG. 6, for example, the therapy annotations 661-664 in the image 660 can be displayed in a first pattern and/or color (e.g., red), whereas the therapy annotation 665 can be displayed in a second pattern and/or color (e.g., blue). In some embodiments, the color and/or pattern of a therapy annotation can be based at least in part on signals received from the sensors 126. For example, the color and/or pattern of an annotation therapy can depend on temperature measurements taken by the sensors 126 on the tip section 124. In these embodiments, the first pattern and/or color of the therapy annotations 661-664 can indicate that sensors 126 of the tip section 124 registered a temperature equal to or greater than a threshold temperature value. In these and other embodiments, the first pattern and/or color can indicate that sensors 126 registered equal to or greater than a threshold temperature value for equal to or greater than a threshold period of time. In these and still other embodiments, the first pattern and/or color can indicate that the integral of temperature difference relative to a minimum threshold temperature at the corresponding location within the anatomical structure 432 was equal to or greater than a minimum threshold temperature integral. In still other embodiments, the first pattern and/or color can indicate merely that therapy was delivered to the anatomical structure 432 at the corresponding location with the tip section 124 of the medical device 104 in a stable position with respect to the anatomical structure 432. In these and other embodiments, the density of the pattern, and/or the color and/or the shade of the color, displayed can change and/or increase, respectively, as temperature increases. In contrast, the second pattern and/or color of the therapy annotation 665 in the image 660 of FIG. 6 can indicate (i) that therapy was either not delivered to the anatomical structure 432 at that location or (ii) that therapy was delivered to the anatomical structure 432 but the therapy did not meet any one or more of the above criteria. Thus, the model 544 can provide an indication of regions in the anatomical structure 432 were therapy delivery was likely insufficient.

In these and other embodiments, the appearance of a therapy annotation can provide an indication of whether therapy was successfully delivered to a region of the anatomical structure 432. For example, therapy annotations can be displayed having one or more specified properties (e.g., shape, size, color, shade, hue, transparency, pattern, etc.) when the interface unit 108 determines that therapy is successfully delivered to a corresponding region of the anatomical structure 432. Whether therapy is successfully delivered to the anatomical structure 432 can depend upon one or more rules (e.g., upon one or more thresholds and/or conditions). For example, the interface unit 108 can monitor one or more signals received from the sensors 126 (e.g., temperature, electrogram characteristics (e.g., amplitude), force, ultrasound, impedance, location (e.g., motion during therapy delivery of lack thereof), shape (e.g., deployment or deformation of the deformable portion 142, etc.)) to determine whether therapy was successfully delivered to a region of the anatomical structure 432. In these and other embodiments, the interface unit 108 can monitor characteristics of therapy delivery (e.g., the duration therapy was delivered, the energy (e.g., power, voltage, current, impedance) delivered, electrodes to which energy was delivered, etc.) in addition to or in lieu of the signals received from the sensors 126 to determine whether therapy was successfully delivered. In the event that the interface unit 108 determines that therapy was not successfully delivered to a corresponding region of the anatomical structure 432, the interface unit 108 can display a therapy annotation lacking the one or more properties indicative of successful therapy delivery and/or can display the corresponding location in the model 544 without a therapy annotation. As such, the model 544 can provide a physician an indication of the progression and/or success of treatment at one or more locations within the anatomical structure 432.

In these and other embodiments, one or more properties of displayed therapy annotations can provide a physician an indication of time of therapy. For example, a pattern, color, shade, hue, and/or transparency of a displayed therapy annotation can indicate how recently the corresponding region of the anatomical structure 432 was treated. Referring to FIG. 6 as a specific example, therapy annotations 661-664 are displayed within the model 544 to indicate that therapy was delivered to regions of the anatomical structure 432 corresponding to the locations of the annotations 661-664. The therapy annotation 664 is displayed with a highlighted third pattern and/or color (e.g., green) outline not shown as part of the therapy annotations 661-663. In some embodiments, this highlighting or another emphasized property (e.g., a pattern) can indicate that a location of the therapy annotation 664 is nearer (based on a distance metric) to the current location of the medical device 104 than the locations of the therapy annotation 661-663. This can provide a physician with additional cues as to the current location of the medical device 104 within the anatomical structure 432 and relative to regions of therapy delivery.

Figure 8:
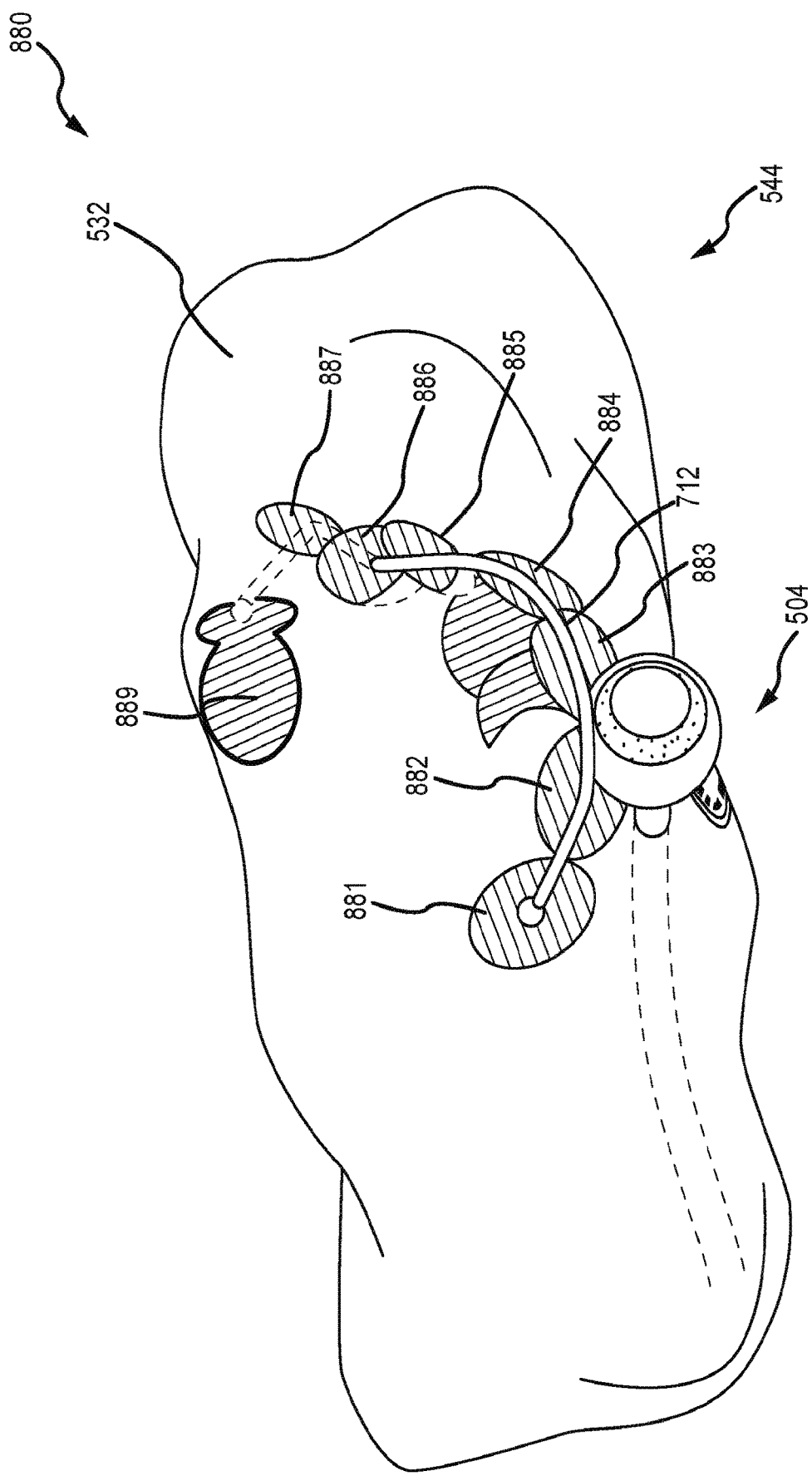

In these and other embodiments, the interface unit 108 can use one or more other properties to distinguish the first therapy delivery location (e.g., along a therapy contour 712) and/or the last therapy delivery location (e.g., along a therapy contour 712) among a group of therapy delivery locations. Referring to FIG. 8, for example, the therapy annotation 889 is displayed highlighted or with another emphasized property (e.g., a pattern) to indicate that the therapy annotation 889 was the last location (e.g., along the therapy contour 712) that therapy was delivered. In other embodiments, the therapy annotation 889 can be highlighted or otherwise emphasized (e.g., with a pattern) to indicate that the therapy annotation 889 was the first location (e.g., along the therapy contour 712 and/or among a group of therapy annotations 881-889) where therapy was delivered. In this manner, the physician is quickly able to track the progression and/or direction of therapy treatment within the anatomical structure 432 and/or to determine an order of discrete therapy regions.

Properties of a therapy annotation can indicate various information in relation to the location of the medical device 104 (e.g., in relationship to the tip section 124 and/or to the deformable portion 142). For example, the pattern density, shade, intensity, hue, and/or transparency of a therapy annotation can be positively or negatively correlated with a distance (based on a distance metric) from the tip section 124 of the medical device 104. That is, as the tip section 124 of the medical device 104 approaches a region of the anatomical structure 432 corresponding to a therapy annotation, the pattern density, shade, intensity, hue, and/or transparency of the therapy annotation can increase or decrease accordingly. As such, the model 544 can provide the physician an indication of treated regions of the anatomical structure 432 proximate the current location of the medical device 104.

In these and other embodiments, therapy annotations can be selectively hidden or displayed based on the location of the tip section 124 of the medical device 104. For example, all or a subset (e.g., a selected number) of therapy annotations within a threshold distance of the tip section 124 can be displayed within the model 544. As a specific example, the interface unit 108 can selectively display one or more nearest therapy annotations to the location of the tip section 124. Referring to FIG. 8 for another example, the spheres displayed in a fourth pattern and/or color (e.g., white) near the representation 504 of the medical device 104 can indicate that the therapy annotations 883 and 884 corresponding to the spheres are near the tip section 124 of the medical device 104. Continuing with this specific example, the sphere corresponding to therapy annotation 889 can also be shown in the fourth pattern and/or color because it is the last therapy annotation.

The distance metric used to determine a distance from a therapy annotation and/or from the medical device 104 can vary relative to (i) a surface normal of the surface 433 of the anatomical structure 432 at the location of the tip section 124 and/or at the location corresponding to a therapy annotation, (ii) a direction of contact or force between the tip section 124 and the surface 433 of the anatomical structure 432, (iii) the current orientation of the tip section 124, and/or (iv) a nearest detected portion of the surface 433 of the anatomical structure 432 (e.g., based on impedance, temperature, ultrasound, etc.). Location offsets in the direction of a surface may be discounted relative to location offsets in a perpendicular direction. Thus, the term "near" can be defined relative to a maximum projected distance normal to the surface 433 of the anatomical structure 432 and/or a maximum fill distance along the surface 433 of the anatomical structure 432.

In these and other embodiments, the interface unit 108 can define a therapy contour 712 (FIG. 7) and can find the nearest point along the therapy contour 712 from the current location of the tip section 124. From that point, the interface unit 108 can find and/or show a subset of the therapy annotations in each direction along the contour 712. As a specific example, the interface unit 108 can find and show two therapy annotations that are adjacent to a nearest point along the therapy contour 712 from the current location of the tip section 124 unless the nearest point is an endpoint of the therapy contour, in which case only one therapy annotation can be found and shown.

The distance metric used to determine a distance (and/or to define "near" and "far") from a therapy annotation and/or from the medical device 104 can depend on multiple location (e.g., position, orientation, and/or shape) signals. For example, the distance can depend on a position and/or orientation of the tip section 124 of the medical device 104. Furthermore, the distance can be defined relative to a point on the surface of the tip section 124 of the medical device 104. Additionally, or alternatively, the distance can depend on a location of one or more of the sensors 126 on the tip section 124 of the medical device 104. Similarly, while the distance can depend on a position of a therapy annotation (e.g., therapy annotation 774), the distance can, additionally or alternatively, depend on one or more locations (e.g., sensor locations) that were used to determine the position of the therapy annotation 774. A distance metric from a first set of one or more locations to a second set of one or more locations can be defined, for example, based on a minimum distance between a first location of the first set of one or more locations and a second location of the second set of one or more locations. Additionally, or alternatively, as described above, such a distance metric can depend on an orientation of a nearby surface 433 of an anatomical structure 432 or on an orientation of the tip section 124 of the medical device 104.

Additionally, or alternatively, the interface unit 108 can display other information regarding the location of the tip section 124 relative to one or more therapy annotations. For example, the distance from the current location of the tip section 124 to the most recent therapy annotation can be displayed within the model. In these and other embodiments, the distance from the current location of the tip section 124 to the nearest therapy annotation can be displayed within the model 544 (as shown in FIGS. 7 and 8). In these and still other embodiments, the distance from the current location of the tip section 124 to a point along the therapy contour 712 can be displayed in the model 544, such as the distance to the midpoint between two adjacent therapy annotations on the contour 712 (e.g., the middle of a gap between the two adjacent therapy annotations).

4. Therapy Contours

Figure 9:
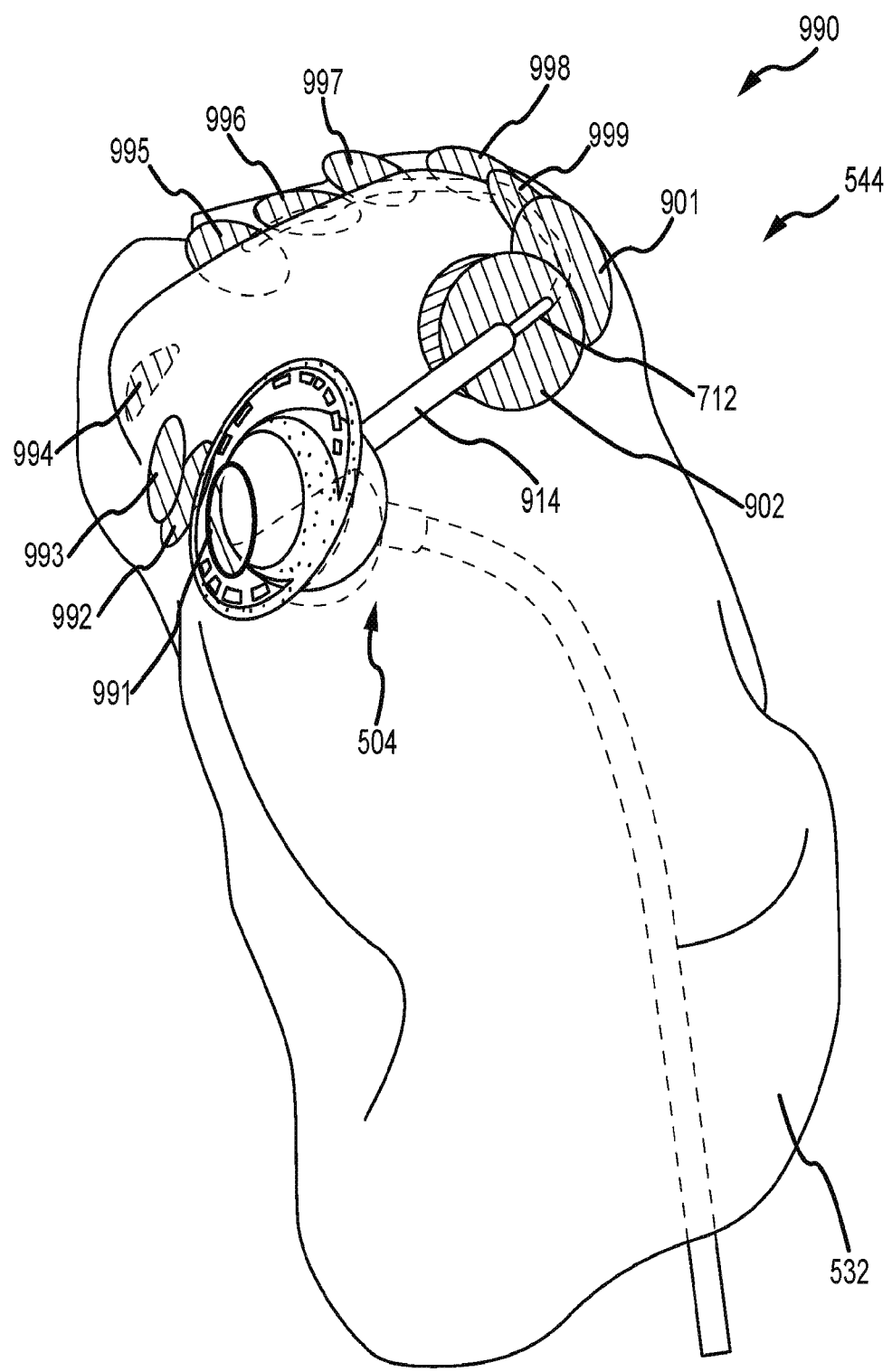

As discussed above, often discrete regions of therapy in point-by-point therapy delivery must be connected to form a contiguous region (e.g., contour, surface, volume, etc.) on an anatomical structure of a patient. Gaps between the discrete regions formed during treatment can decrease the treatment's effectiveness, render the treatment entirely ineffective, and/or lead to other complications. Thus, devices, systems, and methods configured in accordance with various embodiments of the present technology can display one or more therapy contours in addition to or in lieu of displaying therapy annotations in accordance with the above discussion. For example, as shown in FIGS. 7-9, each of the images 770, 880, and 990 include a therapy contour 712 that spans the length of multiple therapy annotations. As used herein, the term "therapy contour" is defined as two or more discrete regions of therapy delivery that are connected (e.g., that are separated by less than a maximum threshold distance, that touch, and/or that at least partially overlap).

To identify, generate, and/or display a therapy contour 712, one or more therapy annotations can be used. For example, the interface unit 108 can define and/or construct a graph in which (i) all or a subset of the therapy annotation locations define vertices and (ii) edges of the graph connect spatially-distributed therapy annotations from disparate therapy delivery events to define spaces between the therapy delivery events. In some embodiments, the Relative Neighborhood Graph (RNG) from a Delaunay triangulation of all or a subset of the annotations can be used to construct the graph. In these and other embodiments, edges that are common to the same therapy delivery element (e.g., edges that connect two therapy annotations from the same therapy delivery event) are considered to contribute zero path length and can be removed from the graph. Additionally, or alternatively, redundant edges (e.g., edges that connect two disparate therapy delivery events that are connected by another edge) can be removed from the graph, keeping the shortest path between the redundant edges.

In some embodiments, the interface unit 108 can find a best open path through the graph. To do so, the interface unit 108 can use Dijkstra's algorithm to find the "longest shortest" path through the graph. For example, for every pair of therapy delivery events represented by annotations in the graph, the interface unit 108 can use Dijkstra's algorithm to find the shortest path length between them, and the interface unit 108 can then define the "longest shortest" path as the longest path in the collection of shortest paths.

In these and other embodiments, the interface unit 108 can find a best closed path or cycle through the graph. For example, the interface unit 108 can calculate an Edge Current Flow Betweenness Centrality of all or a subset of the edges in the graph. In some embodiments, the interface unit 108 can find a cycle that contains the greatest combined edge current flow. Additionally, or alternatively, the interface unit 108 can find a longest cycle.

In these and other embodiments, the best open path and/or the best closed path may not necessarily pass through all of the vertices defined by the therapy delivery events and/or annotation locations. For example, a subset of the therapy delivery locations may be adjacent such that a best open path and/or a best closed path passes through therapy annotations associated with those delivery events, while the best open path and/or the best closed path does not pass through therapy annotations associated with a different subset of the therapy delivery locations.

In some embodiments, the interface unit 108 can be configured to find either the best open path or the best closed path. For example, a physician or user can input or otherwise indicate that therapy is being or will be delivered along an open or closed path, and the interface unit 108 can perform only the calculations corresponding to the selection. In other embodiments, the interface unit 108 can be configured to find both the best open path and the best closed path. In these embodiments, the interface unit 108 can be configured to make a selection between the best open path and the best closed path based on one or more rules. For example, the interface unit 108 can be configured to select the best closed path by default and/or to select the best open path only when the best open path is more than a predetermined factor (e.g., two) larger than the best closed path.

The interface unit 108 can be configured to display the selected best path as a therapy contour 712 alone and/or in combination with associated therapy annotations. In these and other embodiments, the interface unit 108 can be configured to display a therapy surface and/or volume in addition to or in lieu of the therapy contour 712. The interface unit 108 can display a simplified version all or a portion of the graph and/or the selected best path (e.g., as a contour, tube, ribbon, etc.) within the model 544. For example, to generate the display of the therapy contour 712, the interface unit 108 can select therapy delivery events and/or therapy annotations that are on the selected best path and can display a visual indicium that passes through or near the corresponding vertices in the graph and/or through or near the selected therapy annotations. Referring to FIGS. 7-9, for example, the images 770, 880, and 990 include Kochanek spline tube therapy contours 712 that represent respective selected best paths through non-redundant therapy delivery events in the model 544. In this manner, a physician is able to quickly determine whether one or more discrete regions of therapy delivery are included within and/or fall along the therapy contour 712.

In other embodiments, other suitable imaging, contouring, and/or surface generation techniques may be used with images 770, 880, and 990 to display the graph and/or the selected best path. For example, a long, tubular shape with a flattened cross-section can be determined and displayed based on therapy annotations that are part of the graph and/or are on the selected best path. Therapy annotations based on signals indicating tissue proximity and/or successful therapy delivery may lie near a surface corresponding to the surface 433 of the anatomical structure 432. If the therapy annotations fall on or near a surface of an anatomical structure 432, a surface constructed based on the therapy annotations and having a shape with a flattened cross-section may provide an indication of the orientation of the surface of the anatomical structure 432 near the therapy annotations.

Once the best path is selected, calculated, and/or displayed, the interface unit 108 can be configured to highlight or otherwise emphasize (e.g., via patterns) spaces in the graph and visually indicate gaps between therapy delivery events that are included within and/or fall along a therapy contour 712. For example, the interface unit 108 can be configured to modify the displayed properties of non-redundant edges based at least in part on the edge length. As a specific example, to identify such edges, the interface unit 108 can, for each candidate edge on the selected best path that is longer than or equal to a predetermined threshold distance, be configured to (i) attempt to remove the candidate edge from the graph and (ii) determine whether the two vertices in the graph that form the candidate edge remain connected by other edges that are all shorter than the threshold distance. If the two vertices in the graph are not connected by other edges that are all shorter than the threshold distance, the interface unit 108 can highlight the candidate edge.

On the other hand, if the interface unit 108 determines that the two vertices in the graph remain connected by other edges that are all shorter than the threshold distance, the interface unit 108 can be configured to determine whether the selected best path is open. If the interface unit 108 determines that the selected best path is open, the interface unit 108 can not highlight the candidate edge. In these and other embodiments, if the interface unit 108 determines that the selected best path is closed, the interface unit 108 can be configured to determine whether the remaining path length between the two vertices is greater than a predetermined fraction of the total selected best path length. In the event that the interface unit 108 determines that the remaining path length between the two vertices is greater than a predetermined fraction of the total selected best path length, the interface unit 108 can highlight or otherwise emphasize (e.g., via a pattern) the candidate edge. Otherwise, the interface unit 108 does not highlight or otherwise emphasize the candidate edge.

In some embodiments, highlighting or otherwise emphasizing can include displaying the edge (e.g., as a line or cylinder) and/or modifying a corresponding portion of a therapy contour visualization (e.g., with a different pattern, pattern density, color, transparency, diameter, etc.). Referring to FIG. 9, for example, a therapy contour 712 is shown passing through therapy annotations 991-902 within the image 990 of the model 544. A gap exists between therapy annotation 902 and 991. After identifying the gap, the interface unit 108 can modify a corresponding region 914 of the therapy contour 712 to visually depict the gap within the model 544. For example, in the illustrated embodiment, the interface unit 108 has increased the diameter of the region 914 of the therapy contour 712 and has displayed the region 914 in a one pattern and/or color (e.g., blue) instead of the another pattern and/or color (e.g., white). In this manner, a physician is quickly able to determine whether gaps exist between therapy annotations along a therapy contour 712 and/or can determine whether to position the tip section 124 of the medical device 104 over the gap (e.g., between two therapy annotations that are not connected) to deliver therapy and/or form a continuous region of therapy delivery.

5. Therapy Map, Surfaces, and Volumes

Devices, systems, and methods configured in accordance with various embodiments of the present technology can also be configured to display various other visual representations and/or indicia within the model 544. For example, in addition to or in lieu of displaying therapy annotations and/or therapy contours, one or more therapy maps, surfaces, and/or volumes can be displayed within the model 544. The therapy surfaces, volumes, and/or maps can provide a physician an indication of the extent of therapy delivered to the anatomical structure 432 and/or whether discrete regions of therapy delivery are sufficiently connected such that treatment can be considered successful.

Figure 10:
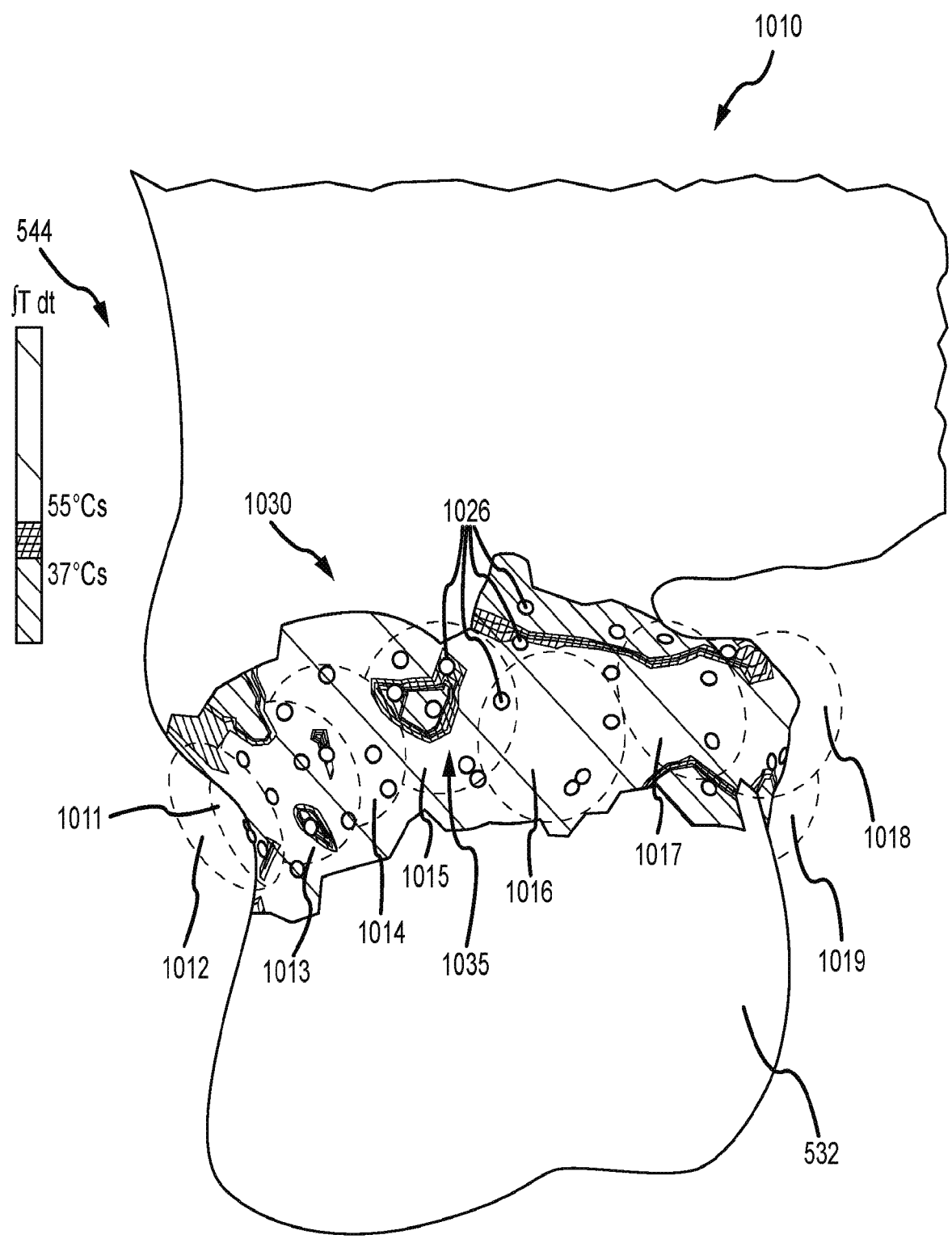

FIG. 10, for example, is an image 1010 of a three-dimensional model 544 displayed on the graphical user interface 110 (FIG. 1) in accordance with various embodiments of the present technology. The model 544 includes a three-dimensional surface representation 532 of an anatomical structure 432. In addition, the model 544 includes several transparent therapy annotations 1011-1019 corresponding to locations of the tip section 124 of the medical device 104 within the anatomical structure 432 when therapy was delivered. In contrast with the embodiments described above, the model 544 illustrated in FIG. 10 also includes projections 526 of a subset of the sensors 126 distributed about the tip section 124 of the medical device 104.

In addition, the model 544 includes a therapy heat map 1030 indicating temperature measurements captured by and/or near the sensors 126 projected onto the representation 532 of the anatomical structure 432. For example, the pattern and/or color coding scheme used to form the therapy heat map 1030 can be based on one or more of the following: maximum temperature, time over a minimum threshold temperature, an integral of temperature difference relative to a minimum threshold temperature, energy delivered, one or more other signals received from the sensors 126 of the medical device 104, and/or one or more other characteristics of therapy delivery (e.g., therapy duration, time of therapy delivery (start time, stop time, how recently therapy was delivered, etc.), etc.). In some embodiments, the term "near" can refer to a maximum projected distance normal to the surface 433 of the anatomical structure 432 and/or a maximum fill distance along the surface 433. In these and other embodiments, the term "near" can be defined using a metric based upon the location and/or orientation of a corresponding therapy annotation.

In this and other embodiments, a therapy map can interpolate values associated with therapy annotations (based on, e.g., maximum temperature, time over a minimum threshold temperature, an integral of temperature difference relative to a minimum threshold temperature, one or more signals received from the sensors 126, one or more other characteristics of therapy delivery, etc.) onto a surface in order to display values between therapy annotations, as shown in FIG. 10. For example, interpolation can be accomplished using radial basis function (RBF) interpolation of values associated with therapy annotations. Interpolation methods can be used to interpolate values based in part on the three-dimensional locations of the corresponding therapy annotations. Alternatively, interpolation methods can be used to interpolate values along the surface based in part on projected locations on the surface of the three-dimensional locations of the corresponding therapy annotations. Interpolation can be accomplished by combining a set of spatial functions centered at each of the therapy annotations to generate a weight for each therapy annotation at each interpolation point on the surface. Spatial functions used to generate weights for interpolation can be based, for example, on a single spatial function that is translated, rotated, and/or scaled based on the value and/or location associated with the corresponding therapy annotation. Additionally, or alternatively, spatial functions used to generate weights for interpolation can vary with respect to a distance metric such as any of the distance metrics described above. An interpolation method can be additive such that a value interpolated onto the surface depends on a weighted sum of values corresponding to nearby (or potentially all) therapy annotations. Alternatively, an interpolation method can be nonlinear such that a value interpolated onto the surface depends on a nonlinear combination (e.g., a maximum, a sum of squares, a specified percentile, etc.) of weighted values corresponding to the therapy annotations.

As discussed above, the therapy map 1030 can provide a physician an indication of the extent of therapy delivered to the anatomical structure 432 and/or whether discrete regions of therapy delivery are sufficiently connected such that treatment can be considered successful. For example, the therapy map 1030 illustrated in FIG. 10 includes a region 1035 corresponding to the location of the therapy annotation 1015. The region 1035 can indicate that the sensors 126 corresponding to the region 1035 did not heat up sufficiently (e.g., did not reach a threshold temperature) and/or did not measure a sufficient temperature increase for a sufficient time period when therapy was delivered to a corresponding region of the anatomical structure 432. Thus, the physician can quickly determine that signals measured during therapy delivery in the region of the anatomical structure 432 corresponding to the region 1035 of the therapy map 1030 indicate that it may not have received adequate therapy (e.g., therapy that successfully prevents signals from propagating through the corresponding tissue). In other words, the physician can quickly locate potential gaps in therapy delivery along a therapy contour by viewing the therapy map 1030. In these embodiments, the physician can, after reviewing signals measured in the region 1035 and/or performing additional confirmation maneuvers, position the tip section 124 of the medical device 104 against the surface 433 of the anatomical structure 432 at a location corresponding to the region 1035 and can deliver therapy to treat the corresponding tissue. In these and other embodiments, the physician viewing the therapy map 1030 illustrated in the FIG. 10 can see that the region 1035 of the therapy map 1030 is surrounded by regions of the anatomical structure 432 in which signals measured during therapy indicate that sufficient therapy was likely delivered (e.g., indicated by one or more densities of patterns and/or one or more selected shades of colors (e.g., red and pink) surrounding the region 1035). Thus, in some embodiments, the physician can determine that the therapy contour illustrated by the therapy map 1030 is sufficiently continuous to indicate successful therapy.

In some embodiments, rather than projecting the therapy map 1030 onto the representation 532 of the surface 433 of the anatomical structure 432 as illustrated in FIG. 10, volume rendering techniques known in the art can be used to render information about spatially distributed therapy annotations. In these and other embodiments, pattern, color, and/or other properties of the rendered volume can vary similarly to the therapy annotations, therapy contours, and/or the therapy maps described above. In these and still other embodiments, volumetric binning and/or smoothing can be used to control the region of influence of each spatially-distributed therapy annotation and/or to smooth the volume rendering.

In other embodiments, rather than projecting or interpolating the therapy map 1030 onto the representation 532 of the surface 433 of the anatomical structure as illustrated in FIG. 10, a therapy map can be projected or interpolated onto a therapy contour or another surface determined based on therapy annotations. Such an approach may reduce errors caused by projecting measurements onto an existing surface.

6. Associated Methods

Figure 11:
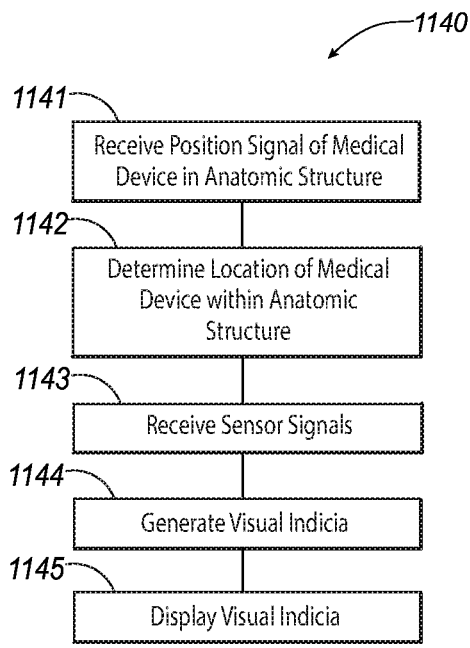
FIG. 11 is a flow diagram illustrating a routine for generating and/or displaying visual indicia regarding therapy delivery in an anatomical structure of a patient in accordance with various embodiments of the present technology.

FIG. 11 is a flow diagram illustrating a routine 1140 for generating and/or displaying visual indicia regarding therapy delivery in an anatomical structure of a patient in accordance with various embodiments of the present technology. All or a subset of the steps of the routine 1140 can be executed by various components or devices of a medical system, such as the system 100 illustrated in FIGS. 1-3 or other suitable systems. For example, all or a subset of the steps of the routine 1140 can be executed by (i) components or devices of an interface unit (e.g., the interface unit 108) and/or (ii) components or devices of a medical device (e.g., the medical device 104). Furthermore, any one or more of the steps of the routine 1140 can be executed in accordance with the discussion above.

The routine 1140 begins at block 1141 by receiving one or more position signals of a medical device in an anatomical structure of a patient. For example, the routine 1140 can receive a position signal of the medical device using one or more imaging techniques and/or sensors (e.g., a magnetic position sensor) of the medical device. In these and other embodiments, the routine 1140 can receive a position signal of the medical device using one or more sensors distributed about a tip section of the medical device.

Based at least in part on the received position signal(s), the routine 1140 at block 1142 determines a location (e.g., position, orientation, and/or shape) of the medical device within the anatomical structure. In some embodiments, the routine 1140 can determine the location (e.g., position, orientation, and/or shape) of the medical device (e.g., of the tip section of the medical device) in relation to the surface of the anatomical structure. For example, the routine 1140 can determine the location of the medical device relative to the surface of the anatomical structure using a generated and/or acquired three-dimensional representation of the anatomical structure and/or by identifying which of the sensors distributed about the tip section of the medical device measure signals indicating proximity to the surface of the anatomical structure.

At block 1143, the routine 1140 continues by receiving one or more sensor signals. For example, the routine 1140 can receive one or more sensor signals from the sensors distributed about the tip section of the medical device. The one or more therapy position signals can indicate portions of the medical device where therapy delivery may have been successful.

At block 1144, the routine 1140 generates visual indicia related to therapy delivered to the anatomical structure. For example, the routine 1140 can generate visual indicia related to therapy delivered to the anatomical structure based at least in part on the one or more sensor signals received at block 1143. In these and other embodiments, the visual indicia can include therapy annotations, therapy maps, therapy surfaces, therapy volumes, therapy contours, and/or other visual indicia (e.g., distance measurements between visual indicia and/or between visual indicia and the medical device).

At block 1145, the routine 1140 displays visual indicia related to therapy delivered to the anatomical structure. For example, the routine 1140 can display a three-dimensional surface representation of the anatomical structure and/or a representation of the medical device (e.g., of the tip section of the medical device) in a model on a graphical user interface. In these and other embodiments, the routine 1140 can display one or more therapy annotations at positions within the model corresponding to the location of the tip section of the medical device when therapy was delivered. In these and still other embodiments, the routine 1140 can display various other visual indicia, such as therapy contours, highlighted and/or emphasized gaps, therapy volumes, therapy surfaces, therapy maps, and/or other information (e.g., the distance to the nearest therapy annotation).

Although the steps of the routine 1140 are discussed and illustrated in a particular order, the routine 1140 illustrated in FIG. 11 is not so limited. In other embodiments, the routine 1140 can be performed in a different order. In these and other embodiments, any of the steps of the routine 1140 can be performed before, during, and/or after any of the other steps of the routine 1140. Moreover, a person of ordinary skill in the relevant art will recognize that the illustrated routine can be altered and still remain within these and other embodiments of the present technology. For example, one or more steps of the routine 1140 illustrated in FIG. 11 can be omitted and/or repeated in some embodiments.

Figure 12:
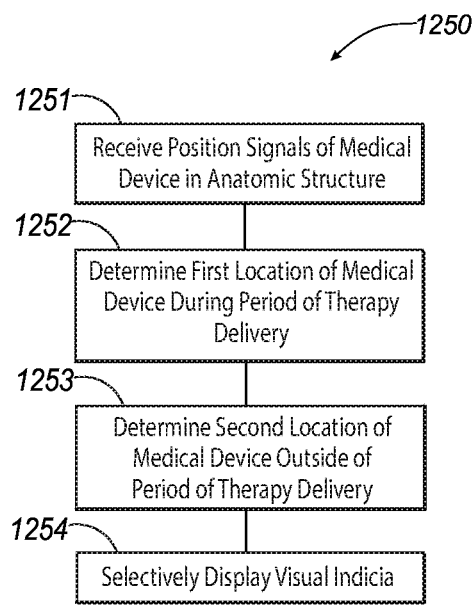
FIG. 12 is a flow diagram illustrating a routine for selectively displaying one or more visual indicia related to therapy delivery within an anatomical structure of a patient in accordance with various embodiments of the present technology.

FIG. 12 is a flow diagram illustrating a routine 1250 for selectively displaying one or more visual indicia related to therapy delivery within an anatomical structure of a patient in accordance with various embodiments of the present technology. All or a subset of the steps of the routine 1250 can be executed by various components or devices of a medical system, such as the system 100 illustrated in FIGS. 1-3. For example, all or a subset of the steps of the routine 1250 can be executed by (i) components or devices of an interface unit (e.g., the interface unit 108) and/or (ii) components or devices of a medical device (e.g., the medical device 104). Furthermore, any one or more of the steps of the routine 1250 can be executed in accordance with the discussion above.

The routine 1250 begins at block 1251 by receiving one or more position signals indicative of a position of a medical device in an anatomical structure of a patient. For example, the routine 1250 can receive a position signal of the medical device using one or more imaging techniques and/or sensors (e.g., a magnetic position sensor) of the medical device. In these and other embodiments, the routine 1140 can receive a position signal of the medical device using one or more sensors distributed about a tip section of the medical device. In these and still other embodiments, the one or more position signals can be indicative of a location (e.g., position, orientation, and/or shape) of a medical device in an anatomical structure of a patient before, during, and/or after therapy is delivered to the anatomical structure.

During a period of therapy delivery, the routine 1250 at block 1252 determines a first location of the medical device within the anatomical structure based at least in part on one or more position signals received at block 1251. In some embodiments, the routine 1250 can determine the first location (e.g., position, orientation, and/or shape) of the medical device (e.g., of the tip section of the medical device) in relation to the surface of the anatomical structure. For example, the routine 1250 can determine the first location of the medical device relative to the surface of the anatomical structure using a generated and/or acquired three-dimensional representation of the anatomical structure and/or by identifying which of the sensors distributed about the tip section of the medical device measure signals indicating proximity to the surface of the anatomical structure.

At block 1253, based at least in part on one or more position signals received at block 1251, the routine 1250 determines a second location of the medical device within the anatomical structure outside the period of therapy delivery. In some embodiments, the routine 1250 can determine the second location of the medical device (e.g., of the tip section of the medical device) in relation to the surface of the anatomical structure. For example, the routine 1250 can determine the second position and/or orientation of the medical device relative to the surface of the anatomical structure using the generated and/or acquired three-dimensional representation of the anatomical structure and/or by identifying which of the sensors distributed about the tip section of the medical device measure signals indicating proximity to the surface of the anatomical structure.

At block 1254, the routine 1250 selectively displays one or more visual indicia on a graphical user interface based at least in part on the first and/or second location of the medical device. In some embodiments, the routine 1250 can selectively display one or more visual indicia based at least in part on the distance between the first and second locations. For example, the routine 1250 can display a therapy contour having one or more properties that vary based at least in part on the distance between the first and second locations. In these and other embodiments, the routine 1250 can display all or a subset of generated visual indicia based at least in part on (i) a distance between the first location and the generated visual indicia and/or (ii) a distance between the second location and the generated visual indicia.

Although the steps of the routine 1250 are discussed and illustrated in a particular order, the routine 1250 illustrated in FIG. 12 is not so limited. In other embodiments, the routine 1250 can be performed in a different order. In these and other embodiments, any of the steps of the routine 1250 can be performed before, during, and/or after any of the other steps of the routine 1250. Moreover, a person of ordinary skill in the relevant art will recognize that the illustrated routine can be altered and still remain within these and other embodiments of the present technology. For example, one or more steps of the routine 1250 (e.g., the block 1251) illustrated in FIG. 12 can be omitted and/or repeated (e.g., after the blocks 1252 and/or 1253) in some embodiments.

D. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A method, comprising:
   receiving a position signal indicating a current position of two or more sensors distributed about a tip section of a catheter within an anatomical structure of a patient;
   receiving at least one therapy delivery signal, wherein the at least one therapy delivery signal includes information related to therapy delivered to a region of the anatomical structure;
   receiving at least one sensor signal from each of the two or more sensors;
   based, at least in part, on the received at least one therapy delivery signal and the received sensor signals,
      determining a weighting of one or more sensors of the two or more sensors that indicate therapy delivery, and/or
      determining a subset of the two or more sensors that indicate therapy delivery;
   based, at least in part, on the received position signal, the received at least one therapy delivery signal, and the determined weighting and/or subset, determining a location of at least one sensor of the two or more sensors;
   generating visual indicia based, at least in part, on the determined location of the at least one sensor of the two or more sensors; and
   selectively displaying the visual indicia on a graphical user interface based, at least in part, on the determined location of the at least one sensor of the two or more sensors.

2. The method of claim 1 wherein:
   the at least one therapy delivery signal includes a first therapy delivery signal;
   the first therapy delivery signal includes information related to therapy delivered to a first region of the anatomical structure;
   determining the location of the at least one sensor of the two or more sensors includes determining the location of the at least one sensor of the two or more sensors when the therapy was delivered to the first region; and
   selectively displaying the visual indicia includes selectively displaying the visual indicia based on a distance between the current position of the two or more sensors and the determined location of the at least one sensor of the two or more sensors when therapy was delivered to the first region.

3. The method of claim 2 wherein the visual indicia includes a therapy annotation corresponding to the determined location of the at least one sensor of the two or more sensors when the therapy was delivered to the first region of the anatomical structure, and wherein selectively displaying the therapy annotation includes displaying the therapy annotation only when the therapy annotation is within a first distance from the current position of the two or more sensors.

4. The method of claim 2 wherein the visual indicia includes a therapy annotation corresponding to the determined location of the at least one sensor of the two or more sensors when the therapy was delivered to the first region of the anatomical structure, and wherein selectively displaying the therapy annotation includes displaying the therapy annotation only when the therapy annotation is a nearest therapy annotation to the current position of the two or more sensors.

5. The method of claim 2 wherein the visual indicia includes a therapy annotation corresponding to the determined location of the at least one sensor of the two or more sensors when the therapy was delivered to the first region of the anatomical structure, and wherein selectively displaying the therapy annotation includes displaying the therapy annotation only when the first region of the anatomical structure is the most recently treated region of the anatomical structure.

6. The method of claim 2 wherein the visual indicia include the distance between the current position of the two or more sensors and the determined location of the at least one sensor when the therapy was delivered to the first region.

7. The method of claim 1 wherein:
the at least one therapy delivery signal includes a first therapy delivery signal and a second therapy delivery signal;
the first therapy delivery signal includes information related to therapy delivered to a first region of the anatomical structure;
the second therapy delivery signal includes information related to therapy delivered to a second region of the anatomical structure;
determining the location of the at least one sensor of the two or more sensors includes (i) determining a location of at least one sensor of the two or more sensors when therapy was delivered to the first region and (ii) determining a location of at least one sensor of the two or more sensors when the therapy was delivered to the second region; and
selectively displaying the visual indicia includes selectively displaying the visual indicia based on a distance between (i) the determined location of the at least one sensor of the two or more sensors when the therapy was delivered to the first region and (ii) the determined location of the at least one sensor of the two or more sensors when the therapy was delivered to the second region.

8. The method of claim 7 wherein:
the visual indicia include—
a first therapy annotation corresponding to the determined location of the at least one sensor of the two or more sensors when the therapy was delivered to the first region of the anatomical structure,
a second therapy annotation corresponding to the determined location of the at least one sensor of the two or more sensors when the therapy was delivered to the second region of the anatomical structure, and
a therapy contour connecting the first therapy annotation and the second therapy annotation;
the method further comprises determining a distance between the first therapy annotation and the second therapy annotation; and
selectively displaying the visual indicia includes—
displaying the therapy contour with a first set of properties when the distance between the first therapy annotation and the second therapy annotation is less than a threshold distance, and
displaying the therapy contour with a second set of properties when the distance between the first therapy annotation and the second therapy annotation is equal to or greater than the threshold distance.

9. The method of claim 8, further comprising determining that the distance between the first therapy annotation and the second therapy annotation is equal to or greater than the threshold distance, wherein—
the visual indicia include a distance from a current position of a first subset of sensors of the two or more sensors to a point on the therapy contour representative of a midpoint between the first therapy annotation and the second therapy annotation; and
selectively displaying the visual indicia includes displaying the distance from the current position of the two or more sensors to the point on the therapy contour representative of the midpoint between the first therapy annotation and the second therapy annotation.

10. The method of claim 8 wherein selectively displaying the therapy contour is further based on a selection between a best open path and a best closed path.

11. The method of claim 1 wherein selectively displaying the visual indicia includes modifying one or more visual properties of the visual indicia, and wherein the one or more visual properties include a size, a shape, an orientation, a highlighting, a color, a shade, a hue, and/or a transparency of the visual indicia.

12. A method, comprising:
receiving a position signal indicating a position of a catheter in an anatomical structure of a patient, wherein the catheter includes a tip section and two or more sensors distributed about the tip section;
receiving a therapy delivery signal;
receiving a temperature signal from each of the two or more sensors;
based, at least in part, on the received temperature signals, determining a weighting of one or more sensors of the two or more sensors that indicate therapy delivery, and/or
determining a subset of the two or more sensors that indicate therapy delivery; and
based, at least in part, on the received position signal, determining a location of at least one of the two or more sensors when therapy was delivered to a region of the anatomical structure;
generating visual indicia based, at least in part, on (i) the determined location of the at least one of the two or more sensors when therapy was delivered to the region of the anatomical structure and (ii) the weighting of the one or more sensors and/or the subset of the two or more sensors.

13. The method of claim 12 wherein the therapy delivery signal includes information related to the therapy delivered to the region of the anatomical structure, and wherein one or more properties of the visual indicia correspond to (i) the determined location of the at least one sensor and (ii) the information related to the therapy delivered to the region of the anatomical structure.

14. The method of claim 12, further comprising determining a current location of the tip section of the catheter based on the received position signal, and wherein one or more properties of the visual indicia correspond to the current location of the tip section.

15. The method of claim 13 wherein the one or more properties of the visual indicia include a location, a size, a shape, an orientation, a highlighting, a color, a shade, a hue, and/or a transparency.

16. The method of claim 12, further comprising receiving at least one sensor signal from each of the two or more sensors, wherein the received sensor signals include an electrogram, a force, an acoustic signal, an impedance, a location, and/or a shape of the tip section.

17. The method of claim 12 wherein:
the therapy delivery signal includes information related to therapy delivered to the region of the anatomical structure;
the information related to the therapy delivered to the region of the anatomical structure includes a time the therapy was delivered to the region of the anatomical structure, a duration the therapy was delivered to the region of the anatomical structure, and/or energy information related to the therapy delivered to the region of the anatomical structure; and
the energy information related to the therapy delivered to the region of the anatomical structure includes power, voltage, current, and/or impedance.

18. The method of claim 12 wherein the visual indicia include a therapy annotation, a therapy contour, a therapy surface, a therapy volume, and/or a therapy map.

19. The method of claim 12 wherein:
the visual indicia include a therapy contour;
the region of the anatomical structure is a first region;
the therapy delivery signal includes information related to therapy delivered to the first region and a second region of the anatomical structure; and
at least one property of the therapy contour depends on a distance between (i) the location of the at least one sensor of the two or more sensors when the therapy was delivered to the first region of the anatomical structure and (ii) a location of the at least one sensor of the two or more sensors when the therapy was delivered to the second region of the anatomical structure.

20. The method of claim 12 wherein the visual indicia include a three-dimensional representation of the anatomical structure and/or a three-dimensional representation of the tip section of the catheter.

21. The method of claim 12, further comprising displaying the visual indicia within a model projected onto a graphical user interface.

22. A method, comprising:
receiving a position signal indicating a position of a catheter in an anatomical structure of a patient, wherein the catheter includes a tip section and two or more sensors distributed about the tip section;
receiving at least one therapy delivery signal, wherein the at least one therapy delivery signal includes information related to therapy delivered to a region of the anatomical structure;
receiving at least one sensor signal from each of the two or more sensors;
based, at least in part, on the received at least one therapy delivery signal and the received sensor signals,
determining a weighting of one or more sensors of the two or more sensors that indicate therapy delivery, and/or
determining a subset of the two or more sensors that indicate therapy delivery;
based, at least in part, on the received position signal, determining a location of at least one sensor of the two or more sensors when the therapy was delivered the region of the anatomical structure; and
generating visual indicia based, at least in part, on (i) the determined location of the at least one sensor and/or (ii) the weighting of the one or more sensors and/or the subset of the two or more sensors.

23. The method of claim 22 wherein the received sensor signals include a temperature, an electrogram, a force, an acoustic signal, an impedance, a location, and/or a shape of the tip section.

* * * * *